United States Patent [19]
Lau et al.

[11] Patent Number: 5,118,599
[45] Date of Patent: Jun. 2, 1992

[54] YELLOW COUPLERS FOR PHOTOGRAPHIC ELEMENTS AND PROCESSES

[75] Inventors: Philip T. S. Lau, Rochester; Danny R. Thompson, Fairport, both of N.Y.; Frederick R. Green, III, Midland, Mich.

[73] Assignee: Eastman Kodak Company

[21] Appl. No.: 651,867

[22] Filed: Feb. 7, 1991

[51] Int. Cl.$^5$ ............................................. G03C 7/36
[52] U.S. Cl. ................................. 430/556; 430/557; 430/558
[58] Field of Search ..................... 430/558, 556, 557

[56] References Cited

U.S. PATENT DOCUMENTS

| | | | |
|---|---|---|---|
| 2,184,303 | 12/1939 | Jennings | 430/376 |
| 2,298,443 | 10/1942 | Weissberger | 430/376 |
| 2,359,274 | 9/1944 | Wilson | 430/376 |
| 2,407,210 | 9/1946 | Weissberger et al. | 430/388 |
| 2,875,057 | 2/1959 | McCrossen et al. | 430/556 |
| 3,265,506 | 8/1966 | Weissberger | 430/556 |
| 3,408,194 | 10/1968 | Loria | 430/548 |
| 3,415,652 | 12/1968 | Porter | 430/557 |
| 3,447,928 | 6/1969 | Loria | 430/548 |
| 3,960,570 | 6/1976 | Oishi et al. | 430/551 |
| 4,268,571 | 5/1981 | Tschopp | 430/556 |
| 4,362,806 | 12/1982 | Whitmore | 430/202 |

FOREIGN PATENT DOCUMENTS 2632401 2/1977 Fed. Rep. of Germany .
9505 12/1894 Switzerland .

OTHER PUBLICATIONS

"Yellow-Forming Colour Couplers", *Research Disclosure*, pp. 90–92, Feb. 1981.

*Primary Examiner*—Lee C. Wright
*Attorney, Agent, or Firm*—Foley & Lardner

[57] ABSTRACT

Novel yellow image dye-forming couplers are disclosed. The couplers comprise an active open-chain keto-methylene group, an anilide group attached to the keto-methylene group, and a cyclic ether group attached to the keto-methylene group. The cyclic ether group comprises two oxygen atoms. Either the anilide group or the cyclic ether may carry a ballast group capable of immobilizing the coupler in the layer in which it is contained. Color photographic elements incorporating the novel couplers are also disclosed.

16 Claims, 4 Drawing Sheets

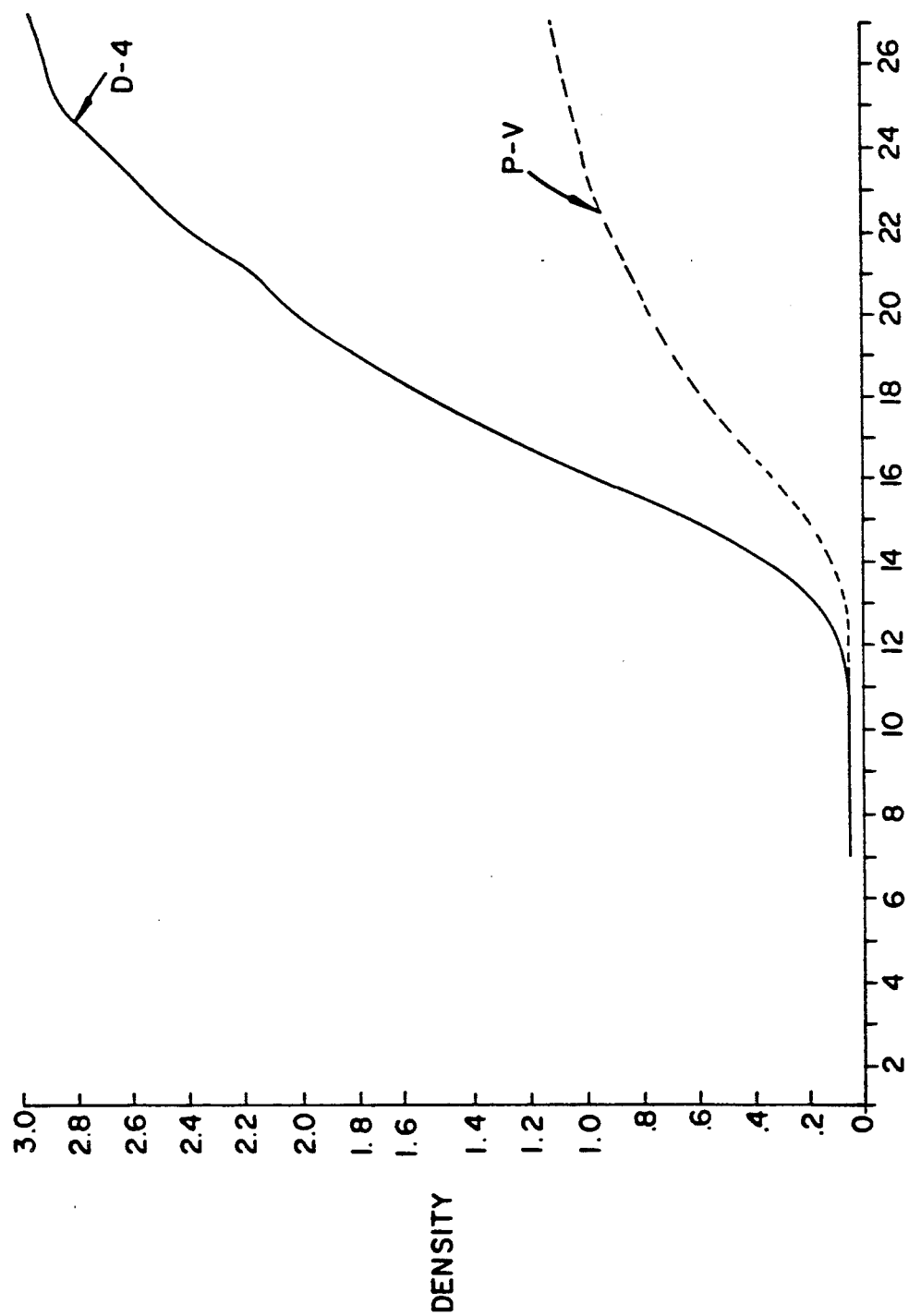

YELLOW COUPLERS FOR PHOTOGRAPHIC ELEMENTS AND PROCESSES

BACKGROUND OF THE INVENTION

This invention relates to novel acetanilide yellow dye-forming couplers and to silver halide photographic elements containing them.

A large number of couplers that provide yellow dye images are known. Couplers that form yellow dyes upon reaction with oxidized color developing agents are typically acylacetanilides. They are described, for example, in Bailey and Williams, "The Photographic Color Development Process" in the CHEMISTRY OF SYNTHETIC DYES (K. Venkataraman, ed.), Academic Press, Inc. New York and London, Vol. 4, 341 (1971). Representative couplers are also described in U.S. Pat. Nos. 2,298,443; 2,407,210; 2,875,057; 3,408,194; 3,265,506; and 3,447,928, and in "Farbkuppler—ein Literaturübersicht," published in AGFA MITTEILUNGEN, Band III, pp. 112-126 (1961).

These compounds contain a reactive methylene group as the coupling function, the functional or reactive group common to coupler compounds which reacts with the development product of a primary aromatic amino developing agent. A reactive methylene is a methylene group which is reactive in the coupling process. For example, the methylene group can be present between two negative centers, as in the group —CO—CH$_2$—CO—.

Two subclasses of acetanilide yellow couplers are commonly used in color photographic film and paper products. One subclass is based on a pivaloyl acetanilide parent and the other is based on a benzoyl acetanilide parent. The 4-equivalent pivaloyl acetanilide-based couplers possess a high pK$_a$ and do not ionize readily at pH 10. Thus, they generally have low coupling activity. This low activity makes these couplers unsuited for use in reversal films.

In reversal films, the amount of silver used in the products cannot be reduced without adversely affecting the granularity of the image dye. Therefore, since excess silver is present in any event, it is advantageous to use four-equivalent couplers in the case of reversal films. These couplers are cheaper to manufacture and have less chemical bulk, due to the absence of the coupling-off group. This decreased bulk permits thinner coatings for improved optical sharpness. A further advantage is the elimination of the processing scum often associated with two-equivalent couplers and caused by the accumulation of the coupling-off groups in the processing solutions.

Conventional four-equivalent yellow couplers do not have sufficient coupling activity for use in reversal film products. For example, the pivaloyl acetanilide-based couplers require reactivity enhancing coupling-off groups when used in reversal films.

SUMMARY OF THE INVENTION

The present invention solves the problem of low coupling activity displayed by conventional yellow pivaloyl acetanilide-based couplers. Because of their high coupling activity, the couplers of our invention can even be used as four-equivalent yellow couplers in a reversal film. Couplers according to the invention are stable, possess superior dye-forming capabilities with or without the need for coupling-off groups and have good dye hue and dye stability. The yellow couplers can be synthesized simply and economically from readily available starting materials and can be substituted with a wide variety of substituents that affect photographic properties, such as dye hue and dye stability.

Yellow couplers according to the invention comprise an active open-chain keto-methylene group, an anilide group attached to the keto-methylene group, and a cyclic ether group attached to the keto-methylene group, the cyclic ether group comprising two oxygen atoms. Preferred couplers according the invention are 1,3-dioxane-5-carbonyl acetanilide couplers represented by the following formula I:

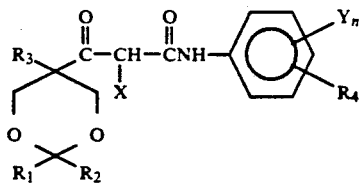

wherein
R$_1$ and R$_2$ are the same or different and may be hydrogen, alkyl, cycloalkyl, bicycloalkyl, aryl, or a ballast group,
R$_3$ is alkyl, aryl, arylalkyl, or a ballast group,
X is hydrogen or a coupling-off group,
Y and R$_4$ are the same or different and may be hydrogen, alkyl, O-alkyl, S-alkyl, SO$_2$-alkyl, SO$_2$NH-alkyl, SO$_2$H-aryl, NHCONH-alkyl, NHCONH-aryl, NHCO-alkyl, CO$_2$-alkyl, O-aryl, SO$_2$-aryl, SO$_2$N(alkyl)-aryl, NHCO-aryl, CO$_2$-aryl, O(CH$_2$CH$_2$O)$_{1-4}$H, COOH, Cl, F, CN, CF$_3$ or NO$_2$, or R$_4$ can be a ballast group, and
n is 0-3.

Color photographic elements comprising couplers according to the invention comprise a support bearing at least one photographic silver halide emulsion layer in association with this image dye-forming coupler.

Other object, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIGS. 3 and 4 are graphs comparing a 4-equivalent coupler according to the present invention to a corresponding pivaloyl acetanilide-based coupler.

DESCRIPTION OF PREFERRED EMBODIMENTS

Figure 1:
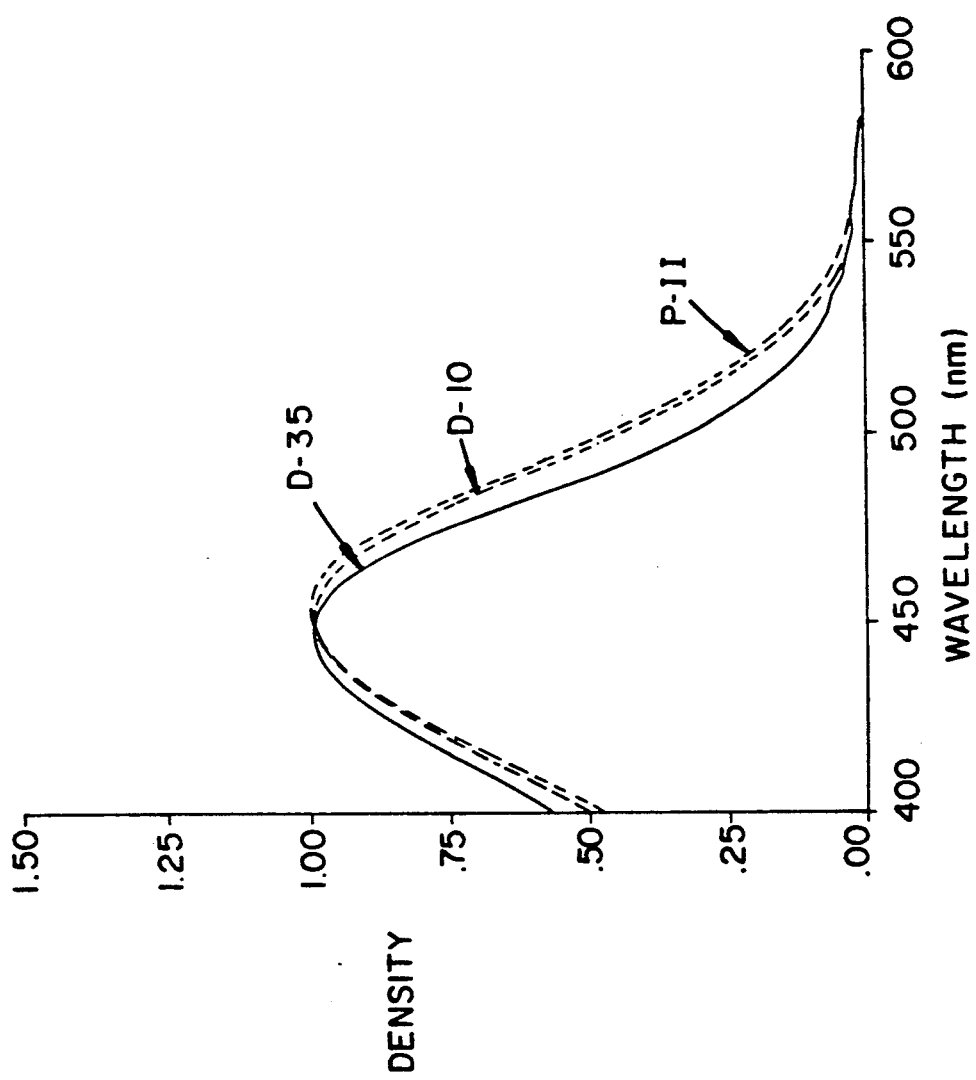
FIG. 1 is a graph comparing the λ$_{max}$ of image dyes derived from couplers according to the present invention and a conventional pivaloyl acetanilide coupler.

A yellow image dye-forming coupler according to the present invention comprises an active open-chain keto-methylene group, an anilide group attached to the keto-methylene group, and a cyclic ether group attached to the keto-methylene group. The cyclic ether group comprises two oxygen atoms. Either the anilide group or the cyclic ether group can comprise a ballast group, i.e., an organic group capable of immobilizing the coupler in the layer in which it is contained.

A preferred acetanilide yellow coupler according to the present invention is based on the 5-alkyl-5-keto-1,3-dioxane acetanilide parent and is described by the following formula I:

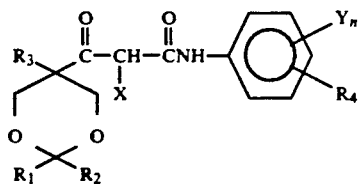
I wherein
- $R_1$ and $R_2$ are the same or different and may be hydrogen, alkyl, cycloalkyl, bicycloalkyl, aryl, or a ballast group,
- $R_3$ is alkyl, aryl, arylalkyl, or a ballast group,
- X is hydrogen or a coupling-of group,
- Y and $R_4$ are the same or different and may be hydrogen, alkyl, O-alkyl, S-alkyl, $SO_2$-alkyl, $SO_2NH$-alkyl, $SO_2NH$-Aryl, NHCONH-Alkyl, NHCONH-Aryl, NHCO-alkyl, $CO_2$-alkyl, O-aryl, $SO_2$-aryl, $SO_2N$(alkyl)-aryl, NHCO-aryl, $CO_2$-aryl, $O(CH_2CH_2O)_{1-4}H$, COOH, Cl, F, CN, $CF_3$ or $NO_2$, or $R_4$ can be a ballast group, and
- n is 0-3.

Preferred groups for $R_1$ and $R_2$ are hydrogen, ($C_1$-$C_{20}$)-alkyl, cycloalkyl, bicycloalkyl, and ($C_6$-$C_{30}$)-aryl, including substituted aryl. Preferred groups for $R_3$ are ($C_1$-$C_{20}$)-alkyl, ($C_6$-$C_{30}$)-aryl or ($C_7$-$C_{30}$)-arylalkyl.

Coupling-off groups, included in the definition of X, are well known to those skilled in the art. Such groups determine equivalency of the coupler. When X is hydrogen in the formula I, i.e., when the methylene is unsubstituted, a four-equivalent coupler results. When X is a so-called coupling-off group (COG), a two-equivalent coupler results. The coupling-off group is eliminated as an anion during development. Coupling-off groups can modify the reactivity of the coupler, or can advantageously affect the layer in which the coupler is coated or other layers in the element by performing, after release from the coupler, such functions as development inhibition, development acceleration, bleach inhibition, bleach acceleration, color correction, and the like. Representative classes of coupling-off groups include halogen, particularly chlorine, bromine and fluorine, alkoxy, aryloxy, heterocyclyloxy, sulfonyloxy, acyloxy, carbonamido, imido, acyl, heterocyclylimido, thiocyano, alkylthio, arylthio, heterocyclythio, sulfonamido, phosphonyloxy and arylazo. They are described, for example, in U.S. Pat. Nos. 2,355,169; 3,227,551; 3,432,521; 3,476,563; 3,617,291; 3,880,661; 4,052,212; and 4,134,766, the disclosure of which are incorporated herein by reference.

Examples of specific coupling-off groups for use in the coupler according to the present invention include:

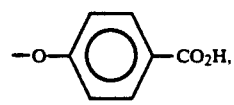

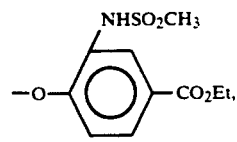

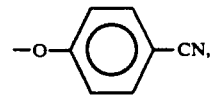

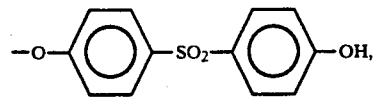

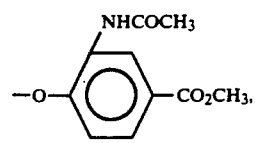

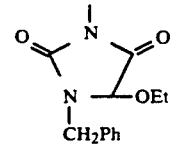

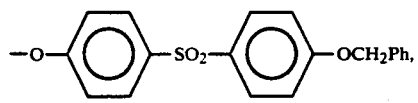

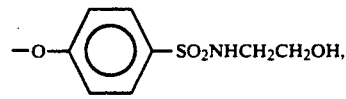

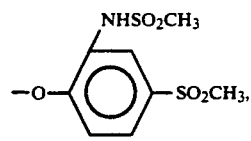

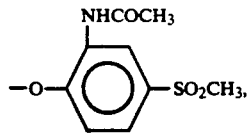

and

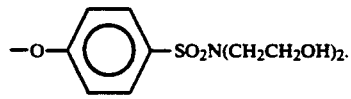

Preferred acetanilide couplers contain a ballast group, an organic group capable of immobilizing the coupler in the layer in which it is contained. This ballast group can be attached either to the acetanilide ring or to the dioxane ring, providing a degree of flexibility not found in other acetanilide couplers.

Representative ballast groups include substituted or unsubstituted alkyl or aryl groups containing 8 to 32 carbon atoms. Typical substituents include alkyl, aryl, alkoxy, aryloxy, alkylthio, arylthio, hydroxy, halogen, alkoxycarbonyl, aryloxycarbonyl, carboxy, acyl, acyloxy, carbonamido, carbamoyl, alkylsulfonyl, arylsulfonyl, sulfonamido, and sulfamoyl groups wherein the alkyl and aryl substituents themselves and portions of the alkoxy, aryloxy, alkylthio, arylthio, alkoxycarbonyl, aryloxycarbonyl, acyl, acyloxy, carbonamido, carbamoyl, alkylsulfonyl, arylsulfonyl, sulfonamido, and sulfamoyl substituents containing 1 to 30 carbon atoms and 6 to 30 carbon atoms, respectively, can be further substituted with such substituents.

In a first embodiment, the anilide group comprises an organic group capable of immobilizing the coupler in the layer in which it is contained and a coupling-off group attached to the active methylene group. These couplers are represented by the following formula II:

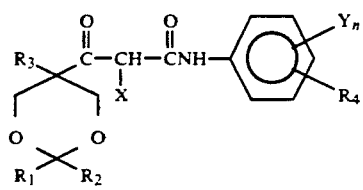

wherein $R_1$ and $R_2$ are the same or different and may be hydrogen, alkyl, cycloalkyl, bicycloalkyl, aryl, or a ballast group, $R_3$ is alkyl or aryl, X is a coupling-off group, Y is hydrogen, alkyl, O-alkyl, S-alkyl, $SO_2$-alkyl, $SO_2NH$-alkyl, $SO_2NH$-aryl, NHCOHN-alkyl, NHCONH-aryl, NHCO-alkyl, $CO_2$-alkyl, O-aryl $SO_2$-aryl, $SO_2N$(alkyl)-aryl, NHCO-aryl, $CO_2$-aryl, $O(CH_2CH_2O)_{1-4}H$, COOH, Cl, F, CN, $CF_3$ or $NO_2$, $R_4$ is a ballast group, and n is 0–3.

Two-equivalent couplers according to formula II are particularly preferred for use in color negative film and color paper.

In a second embodiment, the anilide group again comprises an organic group capable of immobilizing the coupler in the layer in which it is contained, but does not contain a coupling-off group attached to the active methylene group. These couplers are represented by the following formula III:

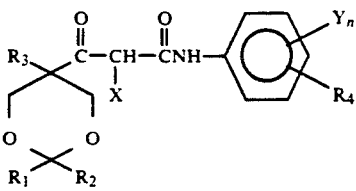

wherein $R_1$ and $R_2$ are the same or different and may be hydrogen, alkyl, cycloalkyl, bicycloalkyl, aryl, or a ballast group, $R_3$ is alkyl or aryl, X is hydrogen, Y is hydrogen, alkyl, O-alkyl, S-alkyl, $SO_2$-alkyl, $SO_2NH$-alkyl, $SO_2NH$-aryl, NHCONH-alkyl, NHCONH-aryl, NHCO-alkyl, $CO_2$-alkyl, O-aryl, $SO_2$-aryl, $SO_2N$(alkyl)-aryl, NHCO-aryl, $CO_2$-aryl, $O(CH_2CH_2O)_{1-4}H$, COOH, Cl, F, CN, $CF_3$ or $NO_2$, $R_4$ is a ballast group, and n is 0–3.

Four equivalent couplers according to formula III are particularly preferred for use in reversal films.

In a third embodiment, the dioxane ring comprises an organic group capable of immobilizing the coupler in the layer in which it is contained. These couplers are represented by the following formula IV:

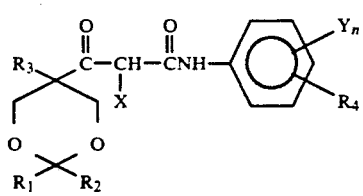

wherein $R_1$ and $R_2$ are the same or different and may be hydrogen, alkyl, cycloalkyl, bicycloalkyl, aryl, or a ballast group, $R_3$ is alkyl, aryl or a ballast group, at least one of $R_1$, $R_2$ or $R_3$ being a ballast group, X is hydrogen or a coupling-off group, Y and $R_4$ are the same or different and may be hydrogen, alkyl, O-alkyl, S-alkyl, $SO_2$-alkyl, $SO_2NH$-alkyl, $SO_2NH$-aryl, NHCONH-alkyl, NHCONH-aryl, NHCO-alkyl, $CO_2$-alkyl, O-aryl, $SO_2$-aryl, $SO_2N$(alkyl)-aryl, NHCO-aryl, $CO_2$-aryl, $O(CH_2CH_2O)_{1-4}H$, COOH, Cl, F, CN, $CF_3$ or $NO_2$, and n is 0–3.

These couplers allow the use of a variety of synthetic handles on the anilide ring.

Examples of representative couplers according to the present invention are shown below.

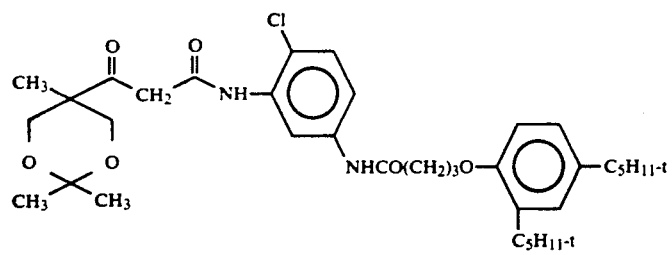
D-0
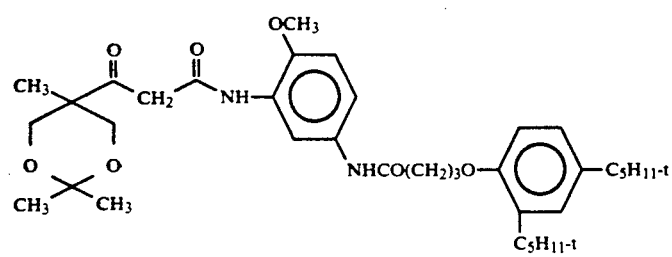
D-1
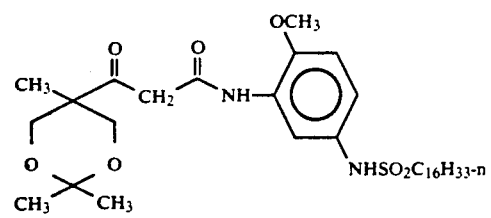
D-2
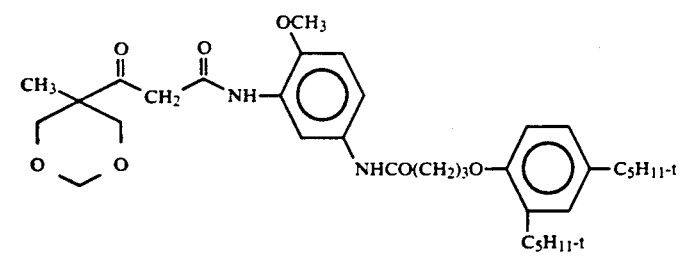
D-3
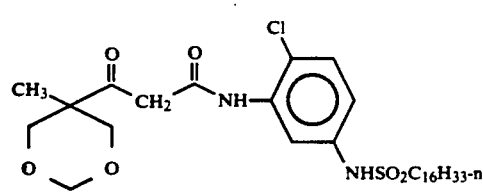
D-4
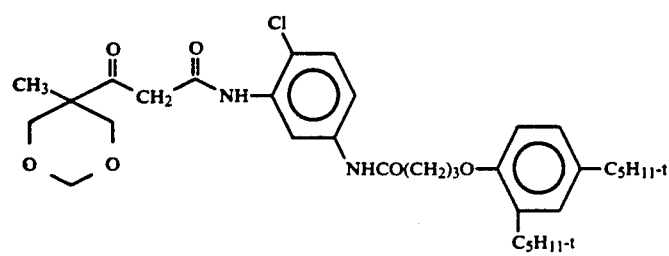
D-5

-continued
D-6
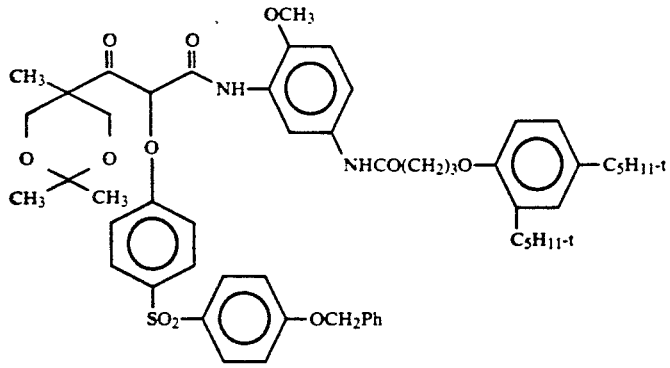
D-7
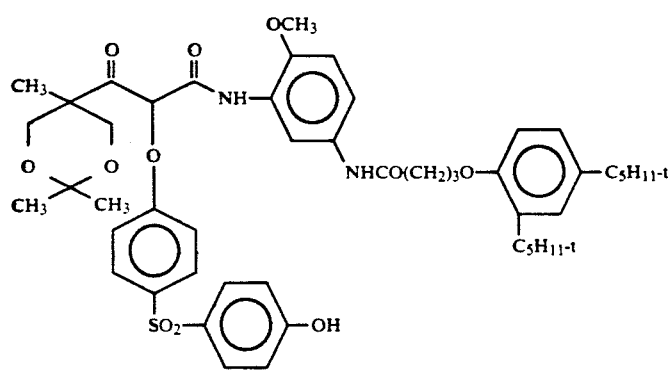
D-8
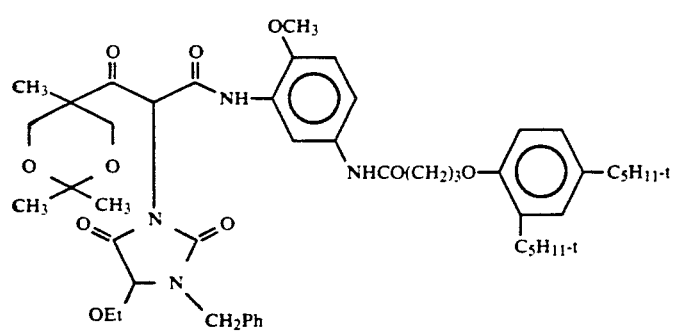
D-9
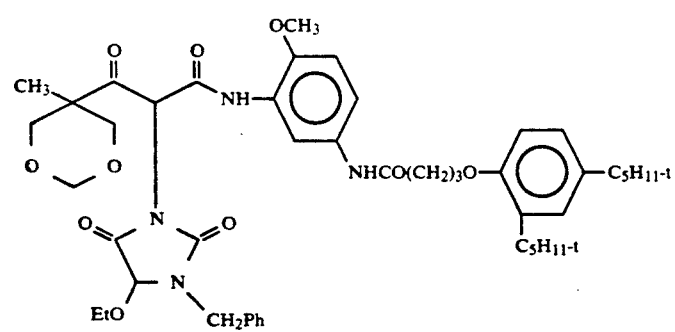
D-10
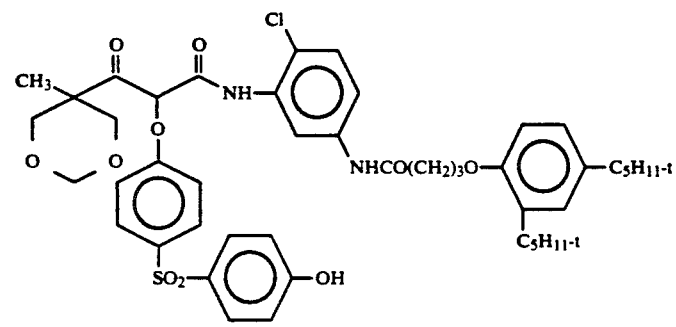

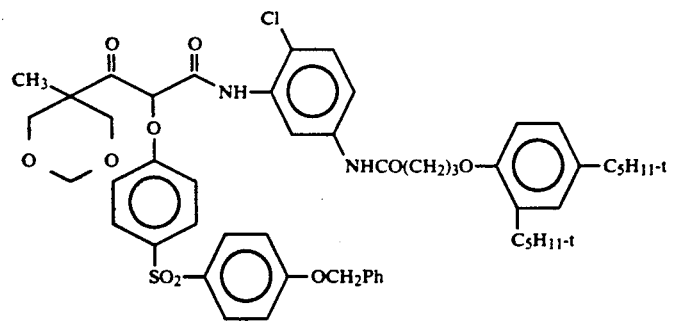
D-11
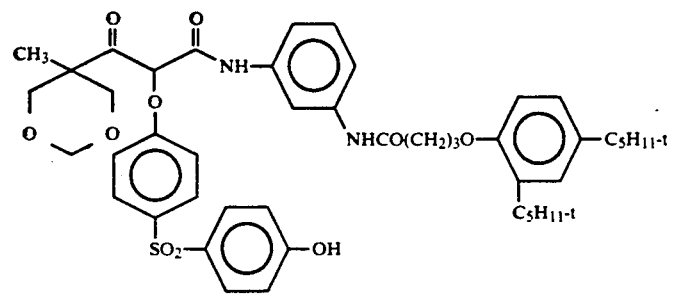
D-12
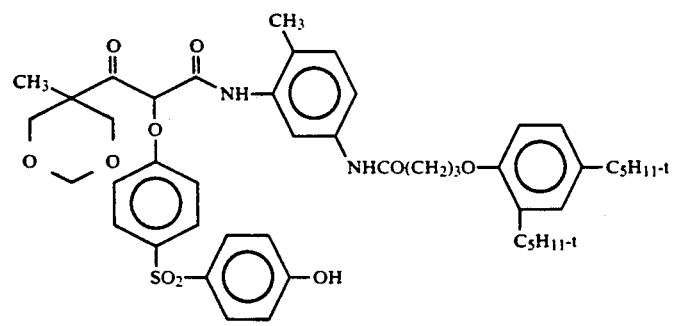
D-13
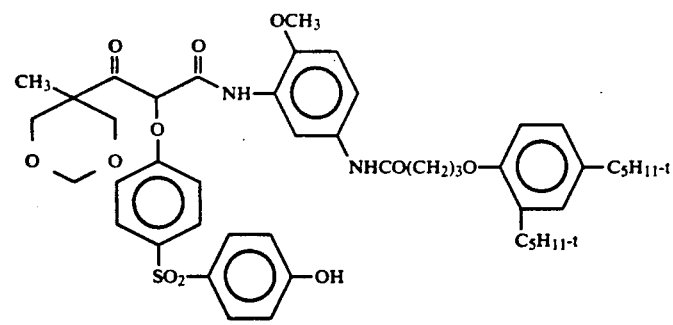
D-14
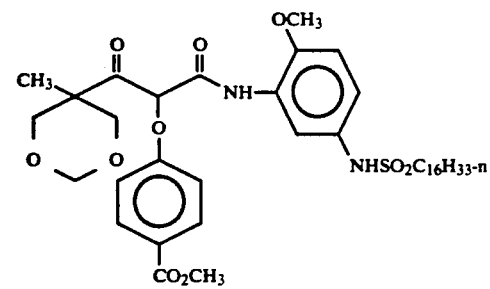
D-15

-continued
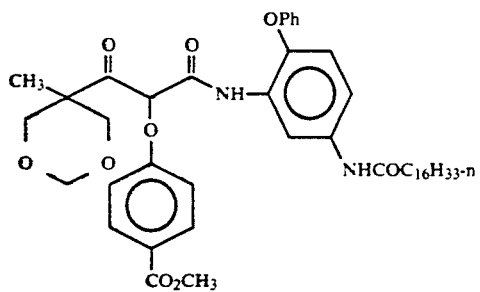
D-16
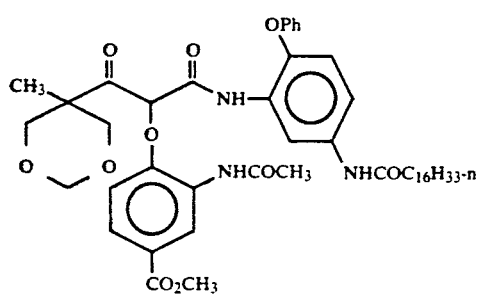
D-17
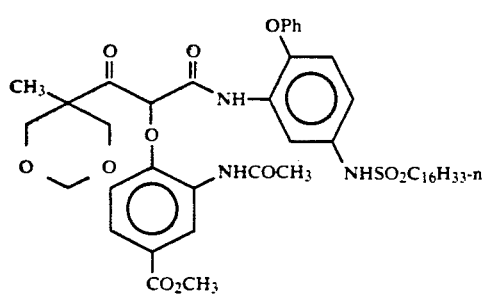
D-18
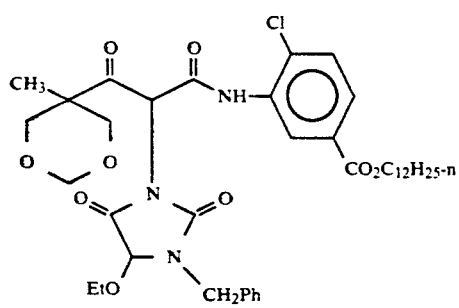
D-19
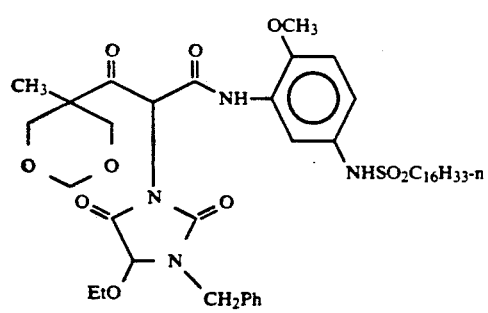
D-20
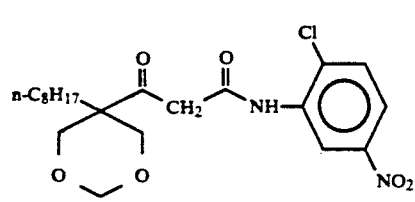
D-21

-continued
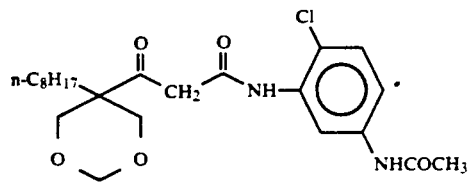
D-22
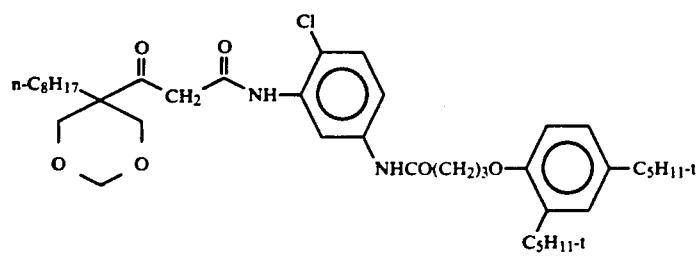
D-23
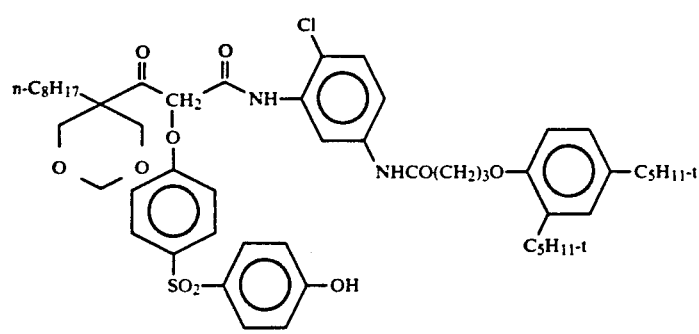
D-24
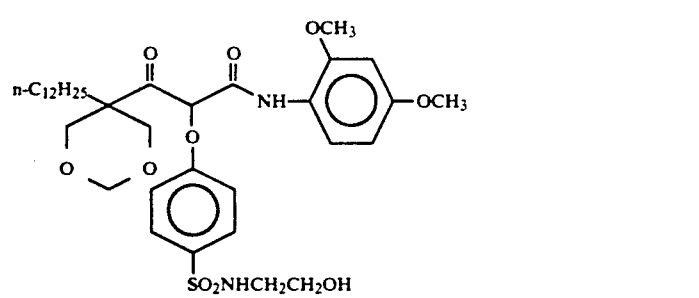
D-25
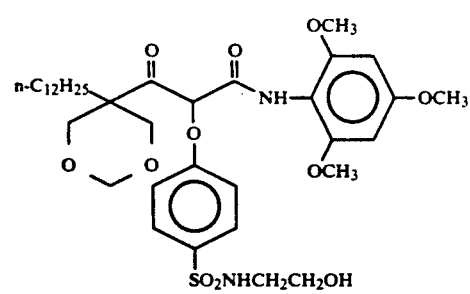
D-26
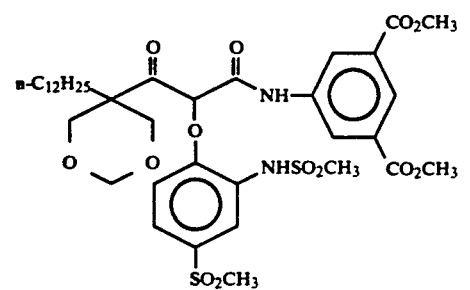
D-27

-continued
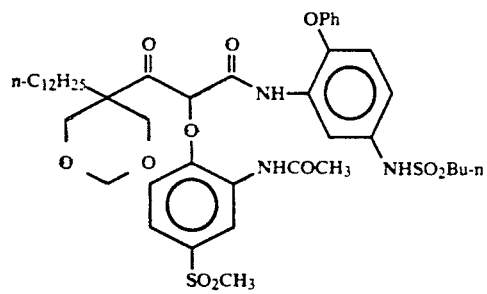
D-28
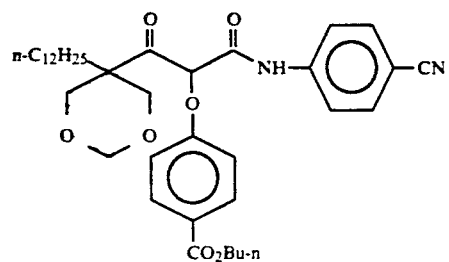
D-29
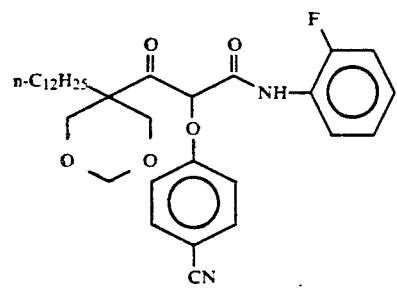
D-30
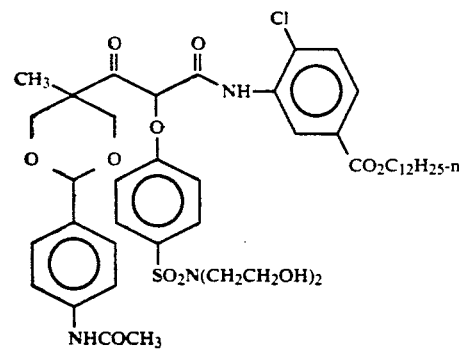
D-31
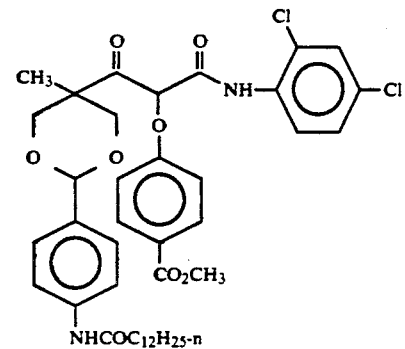
D-32

-continued

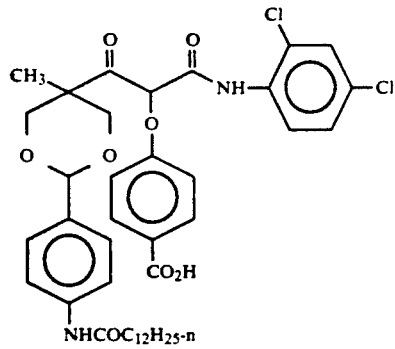
D-33

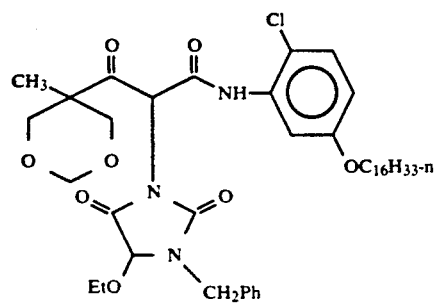
D-34

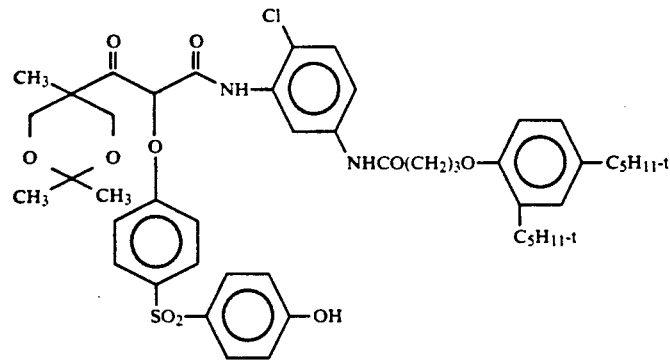
D-35

The yellow coupler according to the present invention possesses unique structural features that give rise to chemical and physical properties not possible for other acylacetanilide-based yellow couplers. The 6-member dioxane ring structure is capable of cis-trans/axial-equatorial isomerization. As a result the degree of solubility of these new couplers in coupler solvents is greatly increased, and dispersions and coatings prepared from them do not show an unwanted tendency to crystallize. Conformational and NMR studies of 5-alkyl-5-acyl-1,3-dioxane systems have shown that the carbonyl group prefers an axial position, thus allowing the carbonyl oxygen to interact with the two oxygen atoms of the 1,3-dioxane ring.

The structural preference of the coupler for the axial conformation has important implications for $pK_2$ values. Due largely to the ability of the carbonyl oxygen to enolize and form H-bonds with the oxygen atoms of the dioxane ring, the $pK_a$ of the coupler is generally 1-2 units lower than pivaloyl acetanilide-based couplers. A lower $pK_a$ value means that the coupler ionizes more readily at pH 10, and results in higher coupling activity with oxidized color developer, as shown in Table 1.

Figure 2:
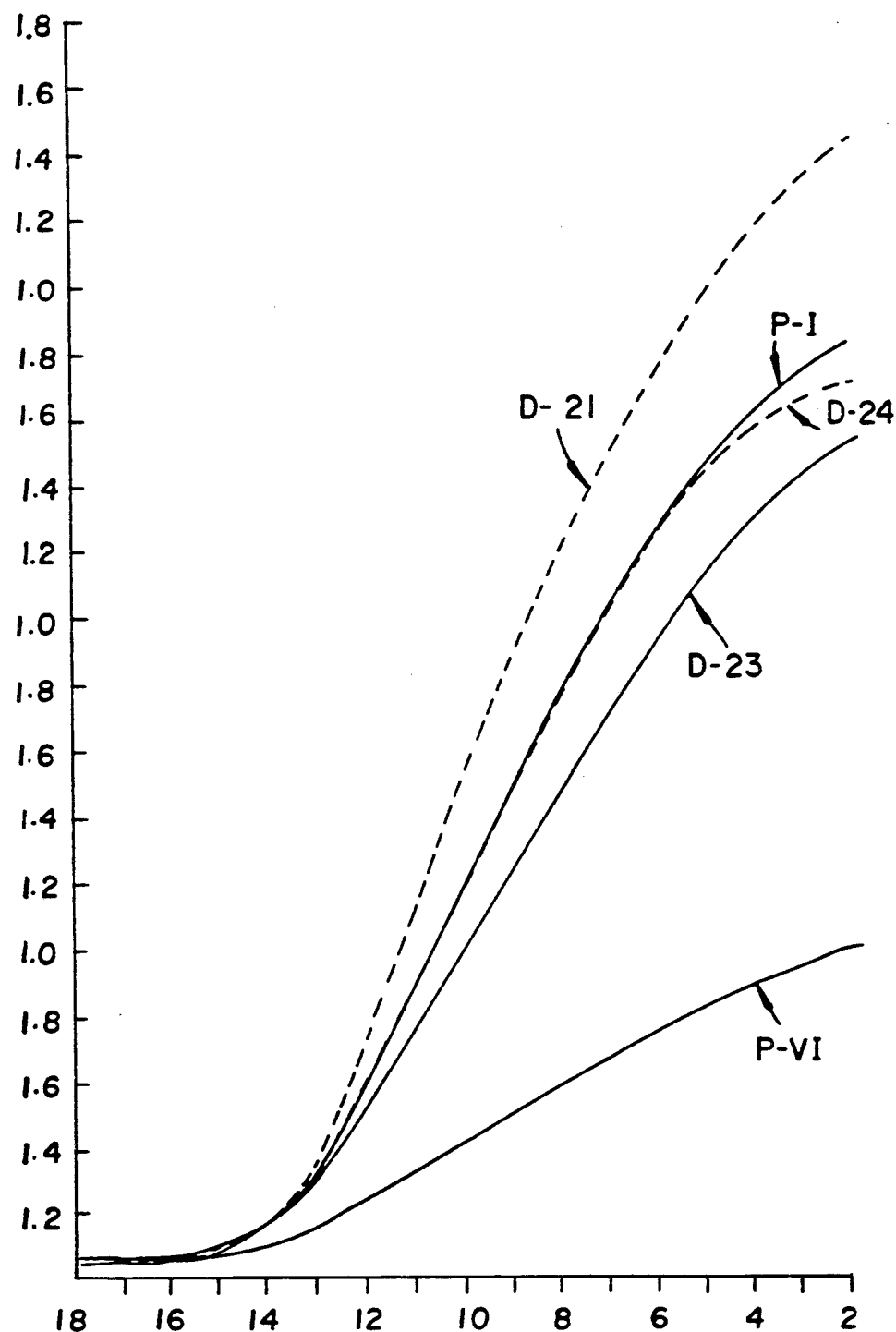
FIG. 2 is a graph comparing couplers according to the present invention having a ballast in the dioxane ring with pivaloyl acetanilide-based couplers.
Figure 3:
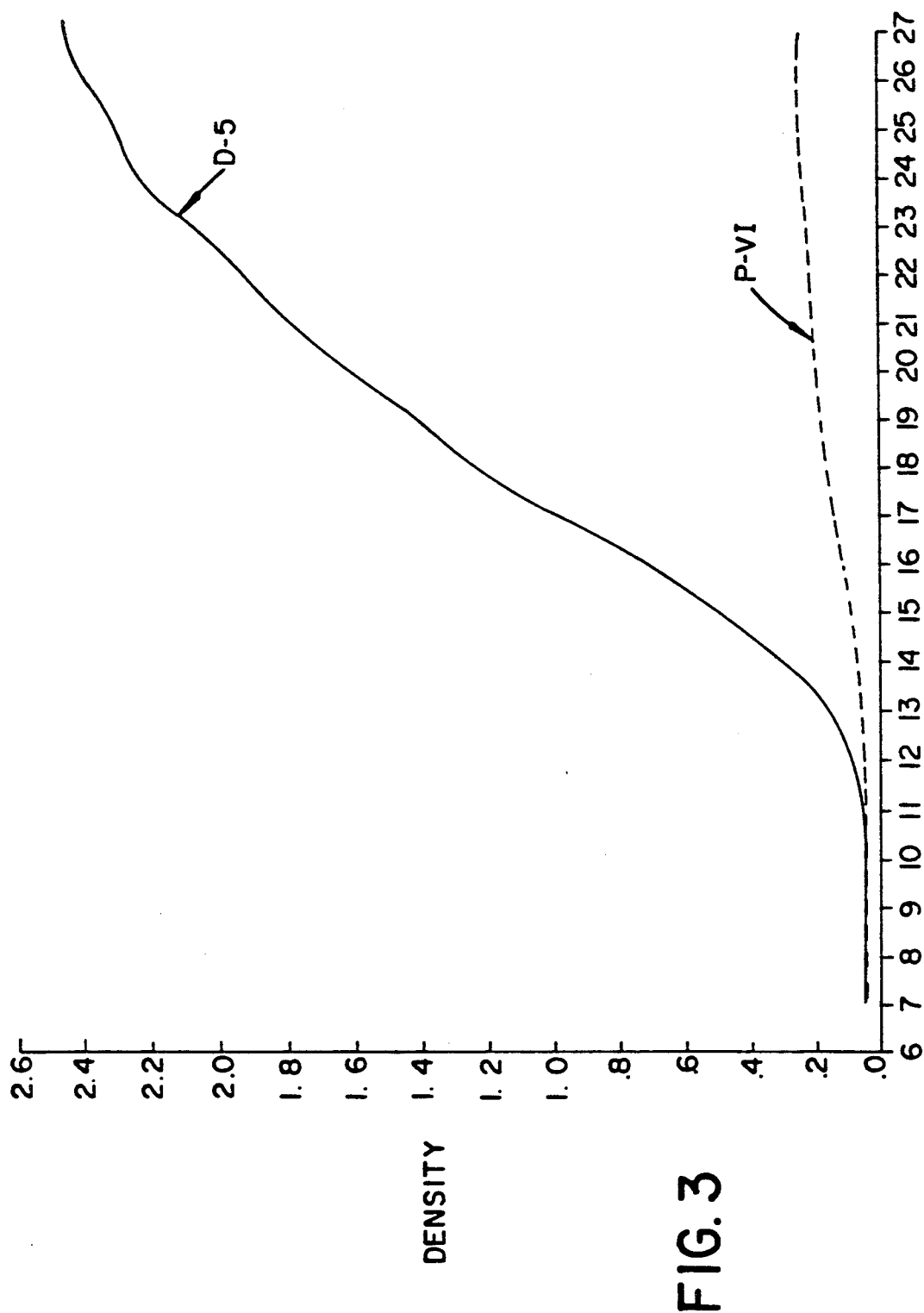

The excellent coupling activity of couplers according to the present invention vis-a-vis pivaloyl acetanilide-based couplers is further shown in FIGS. 2-4. FIG. 2 compares both 2- and 4-equivalent couplers according to the invention having a ballast in the dioxane ring versus comparable pivaloyl acetanilide-based couplers. FIGS. 3 and 4 show the superior activity of a 4-equivalent coupler of the invention versus a corresponding pivaloyl acetanilide-based coupler.

A low $pK_a$ value is especially important when attempting to incorporate substituents into a coupler to affect photographic properties such as dye hue and coupling activity. Since the $pK_a$ of the yellow couplers according to the invention is substantially lower than the pivaloyl acetanilide-based couplers, electron donating substitutions can be made without compromising activity. For example, to reduce the amount of unwanted green absorption of the yellow coupler, it is desirable to shift the dye hue 2-3 nm hypsochromic relative to commercially available pivaloyl acetanilide yellow couplers used in current photographic films and papers. Since couplers according to the invention have lower $pK_a$ values, the hues can be shifted to shorter wavelength by means of electron-donating groups, e.g., methoxy, in the anilide ring without sacrificing coupling reactivity.

TABLE 1

$pK_a$ Measurements

TABLE 1-continued

P-Class structure: (CH₃)₃C-CO-CH(X)-CO-NH-(2-Cl-phenyl)-NHCO(CH₂)₃O-(2,4-di-tert-pentylphenyl)

D-Class structure: dioxane-substituted with CH₃ and R,R groups, -CO-CH(X)-CO-NH-(2-Cl-phenyl)-NHCO(CH₂)₃O-(2,4-di-tert-pentylphenyl)

| Coupler | X | R | pK$_a$ |
|---------|---|---|--------|
| P-VI | H | — | 10.01 |
| D-0 | H | CH₃ | 8.51 |
| D-4 | H | H | 8.42 |
| P-III | -O-C₆H₄-SO₂-C₆H₄-OCH₂Ph | — | 8.76 |
| D-11 | " | H | 7.24 |
| P-II | -O-C₆H₄-SO₂-C₆H₄-OH | — | 9.69 |
| D-10 | " | H | 7.55 |

TABLE 2

Effect of Substituents on $\lambda_{max}$ (D99)

Structure: dioxane (CH₃, OCH₂O) – CO – CH(X) – CO – NH – (2-Y-phenyl) – NHCO(CH₃)₃O – (2,4-di-tert-pentylphenyl)

| | | Y | | |
|---|---|---|---|---|
| X | H | Cl | CH₃ | OCH₃ |
| -O-C₆H₄-SO₂-C₆H₄-OCH₂Ph | 453.4 nm | 453.2 nm | 449.9 nm | 447.0 nm |
| -O-C₆H₄-SO₂-C₆H₄-OH | 453.8 | 453.1 | 450.7 | 448.2 |
| hydantoin (EtO, CH₂Ph) | 452.6 | 451.8 | 448.7 | 446.2 |

Image dyes derived from the coupler according to the present invention have dye hues similar to that of pivaloyl acetanilide-based couplers, with $\lambda_{max}$ ranging from 445 to 455 nm. See FIG. 1 and Table 2. Depending upon the nature of the substituents on the anilide ring or the coupling-off groups (see Table 2) or the substituents on the dioxane ring (see FIG. 1) the dye hue can be modified as desired.

A significant advantage which these couplers enjoy over the pivaloyl acetanilide-based couplers is the availability of a large number of synthetic handles for controlling and improving photographic properties, such as dye hue and dye stability. For example, the ballast group can be present on either or both of the anilide ring or the dioxane ring. By placing the ballast group on the dioxane ring, the anilide ring is free for other substitutions.

A coupler according to the present invention can be prepared conveniently and inexpensively from commercially available starting materials. The following representative reaction scheme shows synthesis of a coupler according to the present invention.

Reaction Scheme

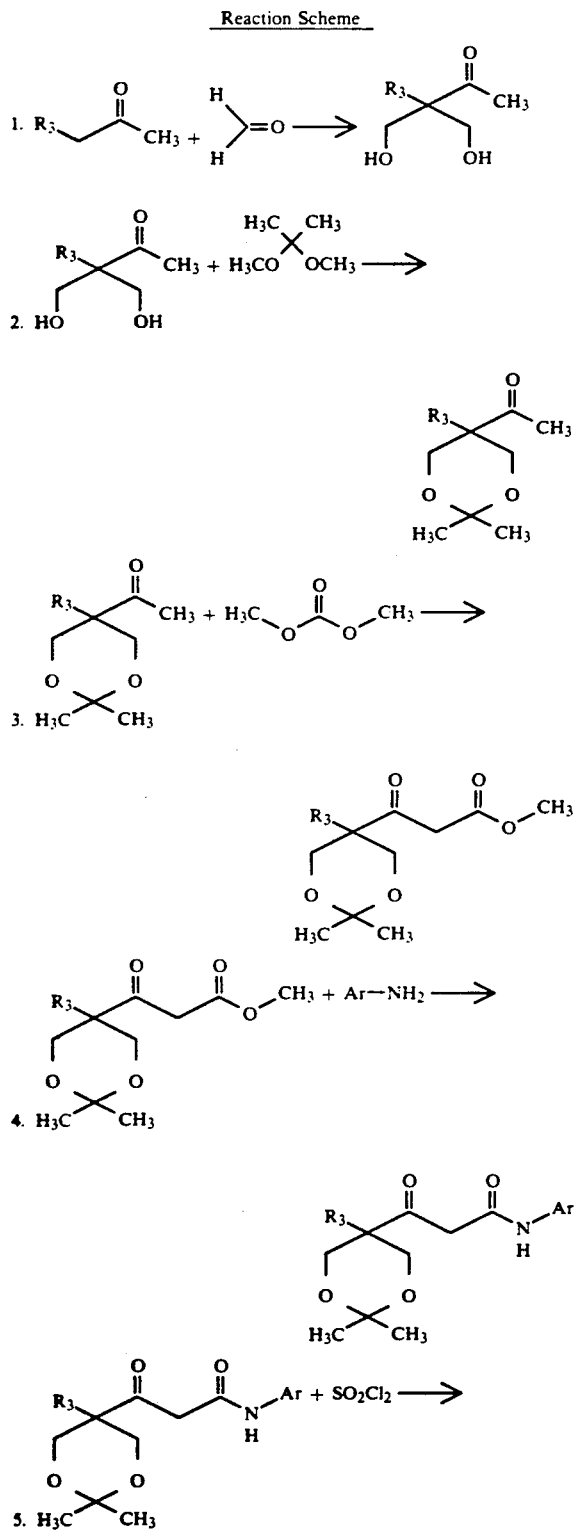

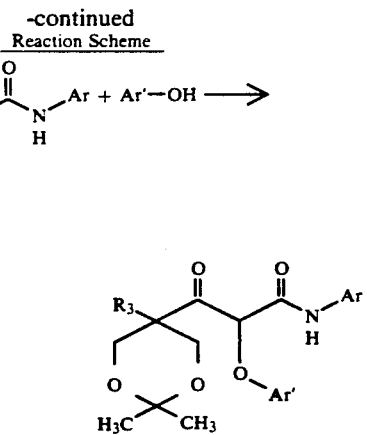

Preferably, the couplers according to the invention are incorporated in silver halide emulsions and the emulsions are coated on a support to form a photographic element. Alternatively, the inventive couplers can be incorporated in photographic elements adjacent the silver halide emulsion where, during development, the coupler will be in reactive association with development products such as oxidized color developing agent. Thus, as used herein, the term "associated therewith" signifies that the coupler is in a silver halide emulsion layer or in an adjacent location where, during processing, it will come into reactive association with silver halide development products. The amount of coupler to be incorporated in an emulsion is generally between about 0.15 and 0.25 mmol/ft$^2$. Unballasted couplers can be used in a Kodachrome-type process.

Photographic elements in which the coupler according to the invention is incorporated can be simple elements comprising a support and a single silver halide emulsion layer, or they can be multilayer, multicolor elements. The silver halide emulsion layer can contain or have associated therewith other photographic coupler compounds, such as colored masking couplers or competing couplers. These other photographic couplers can form dyes of the same or different color and hue as the couplers according to the invention. In addition, the silver halide emulsion layers and other layers of the photographic element can contain other conventional additives.

The photographic elements can be single color elements or multicolor elements. In a multicolor element, the yellow dye image-forming coupler of this invention would usually be associated with a blue-sensitive emulsion, although it could be associated with an emulsion sensitized to a different region of the spectrum, or with a panchromatically sensitized, an orthochromatically sensitized or an unsensitized emulsion. Multicolor elements contain dye image-forming units sensitive to each of the three primary regions of the spectrum. Each unit can comprise a single emulsion layer or multiple emulsion layers sensitive to a given region of the spectrum. The layers of the element, including the layers of the image-forming units, can be arranged in various orders known to those skilled in the art. In an alternative format, the emulsions sensitive to each of the three primary regions of the spectrum can be disposed as a single segmented layer, e.g., as by the use of microvessels as described in Whitmore, U.S. Pat. No. 4,362,806, issued Dec. 7, 1982. A typical multicolor photographic element can also contain additional layers, such as filter layers, interlayers, overcoat layers, subbing layers and the like.

A typical multilayer, multicolor photographic element would comprise a support bearing a yellow dye image-forming unit comprising at least one blue-sensitive silver halide emulsion layer having associated therewith at least one yellow dye-forming coupler, at least one of the yellow dye-forming couplers being a coupler according to the present invention. The element would additionally comprise a red-sensitive silver halide emulsion unit having associated therewith a cyan dye image-forming material and a green-sensitive silver-halide emulsion unit having associated therewith a magenta dye image-forming material. Each silver halide emulsion layer can comprise one or more layers. Various arrangements of the units and layers are possible.

The light-sensitive silver halide emulsions can include coarse, regular or fine grain silver halide crystals or mixtures thereof and can comprise such silver halides as silver chloride, silver bromide, silver bromoiodide, silver chlorobromoiodide and mixtures thereof. They can form latent images predominantly in the surface of the silver halide grains or predominantly in the interior of the silver halide grains. The emulsions can be negative-working emulsions, such as surface-sensitive emulsions or unfogged internal latent image-forming emulsion, or direct-positive emulsions of the unfogged, internal latent image-forming type, which are positive-working when development is conducted with uniform light exposure or in the presence of a nucleating agent.

The silver halide emulsions can be chemically and spectrally sensitized. The emulsions typically will be gelatin emulsions although other hydrophilic colloids are also useful.

The support can be any support used with photographic elements. Typical supports include cellulose nitrate film, cellulose acetate film, polyvinylacetal film, polyethylene terephthalate film, polycarbonate film and related films or resinous materials, as well as glass, paper, metal and the like. Typically, a flexible support is employed, such as a polymeric film or paper support. Paper supports can be acetylated or coated with baryta and/or an α-olefin polymer, particularly a polymer of an α-olefin containing 2 to 10 carbon atoms such as polyethylene, polypropylene, ethylene-butene copolymers and the like.

Suitable materials for use in the emulsions and elements according to the invention are described in *Research Disclosure*, Dec. 1989, Item 308119, published by Kenneth Mason Publications Ltd., Elmsworth, Hampshire PO10 7DQ, U.K., the contents of which are incorporated in their entireties herein by reference. This publication describes both negative-working and positive-working silver halide emulsions, conventional couplers which can be used in addition to the couplers according to the invention, and suitable additives, such as brighteners, antifoggants and stabilizers, antistain agents and image dye stabilizers, light-absorbing and scattering materials, hardeners, plasticizers and lubricants, antistatic agents, matting agents and development modifiers, as well as a variety of supports on which the photographic layers can be coated.

Photographic elements are exposed to actinic radiation, typically in the visible region of the spectrum, to form a latent image and then processed to form a visible dye image. Processing to form a visible dye image includes the step of contacting the element with a color developing agent to reduce developable silver halide and oxidize the color developing agent. Oxidized color developing agent in turn reacts with the coupler to yield a dye.

Preferred color developing agents are p-phenylene diamines. Especially preferred are 4-amino-N,N-diethylaniline hydrochloride, 4-amino-3-methyl-N,N-diethylaniline hydrochloride, 4-amino-3-methyl-N-ethyl-N-β-(methanesulfonamido)ethylaniline sulfate hydrate, 4-amino-3-β-(methanesulfonamido)ethyl-N,N-diethylaniline hydrochloride and 4-amino-N-ethyl-N-(2-methoxyethyl)-m-toluidine di-p-toluenesulfonic acid.

With negative-working silver halide this processing step leads to a negative image. To obtain a positive (or reversal) image, this step can be preceded by development with a non-chromogenic developing agent to develop exposed silver halide, but not form dye, then uniformly fogging the element to render unexposed silver halide developable, followed by development with a chromogenic developer. Alternatively, a direct-positive emulsion can be employed to obtain a positive image. Development is followed by the conventional steps of bleaching, fixing, or bleach-fixing, to remove silver and silver halide, followed by washing and drying.

Several factors influence the choice of four-equivalent or two-equivalent couplers to be used. Four-equivalent couplers are cheaper to make and are less bulky, due to the absence of the coupling-off group. This permits thinner coatings for improved optical sharpness. A further advantage of four-equivalent couplers is the elimination of the processing scum often associated with two-equivalent couplers and caused by the accumulation of the coupling-off groups in the processing solutions.

On the other hand, two-equivalent couplers offer the advantage of a savings in silver. But with certain color photographic products, such as reversal films, the amount of silver used in the products cannot be reduced without adversely affecting the granularity of the image dye, and it would be advantageous, therefore, to use the less-expensive four-equivalent couplers. But conventional four-equivalent pivaloyl acetanilide-based yellow couplers do not have sufficient coupling activity for use in reversal film products.

The four-equivalent couplers according to the present invention have sufficient coupling activity for use in reversal film products, giving dye density yields approaching those of active two-equivalent pivaloyl acetanilide-based couplers. See Table 3.

TABLE 3

| Coupler | D99, pH 10.0, KS-2 | | | |
|---|---|---|---|---|
| | Dmax | Dmin | γ | λmax |
| P-VI | 0.25 | 0.05 | 0.10 | 447 |
| P-V | 1.11 | 0.06 | 0.43 | 449 |
| D-5 | 2.46 | 0.05 | 0.83 | 452 |
| D-4 | 2.95 | 0.06 | 1.10 | 454 |
| D-2 | 1.92 | 0.06 | 0.60 | 446 |

Accordingly, a four-equivalent coupler represented by the following formula III is particularly preferred for use in reversal films:

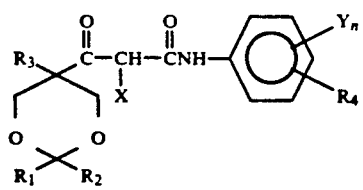

wherein
$R_1$ and $R_2$ are the same or different and may be hydrogen, alkyl, cycloalkyl, bicycloalkyl, aryl, or a ballast group,
$R_3$ is alkyl or aryl,
X is hydrogen,
Y is hydrogen, alkyl, O-alkyl, S-alkyl, $SO_2$-alkyl, $SO_2NH$-alkyl, $SO_2NH$-aryl, NHCONH-alkyl, NHCONH-aryl NHCO-alkyl, $CO_2$-alkyl, O-aryl, $SO_2$-aryl, $SO_2N$(alkyl)-aryl, NHCO-aryl, $CO_2$-aryl, $O(CH_2CH_2O)_{1-4}H$, COOH, Cl, F, CN, $CF_3$ or $NO_2$, and
$R_4$ is a ballast group, and
n is 0-3.

For use in color negative films and color paper, a two-equivalent coupler according to the following formula II is preferred:

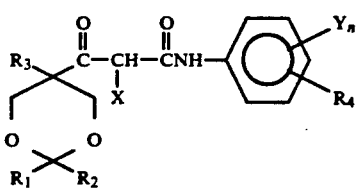

wherein
$R_1$ and $R_2$ are the same or different and may be hydrogen, alkyl, cycloalkyl, bicycloalkyl, aryl, or a ballast group,
$R_3$ is alkyl or aryl,
X is a coupling off group, Y is hydrogen, alkyl, O-alkyl, S-alkyl, $SO_2$-alkyl, $SO_2NH$-alkyl, $SO_2NH$-aryl, NHCONH-alkyl, NHCONH-aryl, NHCO-alkyl, $CO_2$-alkyl, O-aryl, $SO_2$-aryl, $SO_2N$(alkyl)-aryl, NHCO-aryl, $CO_2$-aryl, $O(C_2H_2O)_{1-4}H$, COOH, Cl, F, CN, $CF_3$ or $NO_2$, and $R_4$ is a ballast group; and n is 0-3.

The following examples illustrate the synthesis of particular couplers according to the invention, and use of exemplary couplers in photographic films.

SYNTHETIC PROCEDURES 3,3-bis(Hydroxymethyl)-($R_3$)-2-one

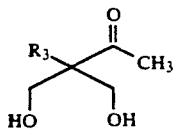
(1)

[$R_3$]-3,3-bis(hydroxymethyl) methyl ketones of the general structural formula (1) are either known compounds or can be prepared from appropriate methyl ketones of the structural type (2)

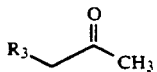
(2)

where $R_3$ is methyl, ethyl, higher or branched alkyl, aryl, substituted aryl, cycloalkyl, bicycloalkyl, etc., by a catalyzed condensation of ketone (2) with formaldehyde (formalin) in an appropriate solvent. More specifically the condensation reaction is performed in a solvent, in the presence of a catalyst, with heating or cooling as necessary. Catalysts include, but are not necessarily limited to, lithium hydroxide, potassium carbonate and calcium hydroxide, with the latter being preferred. Suitable solvents are water, aqueous ethyl alcohol or other aqueous media, Representative Reaction I.

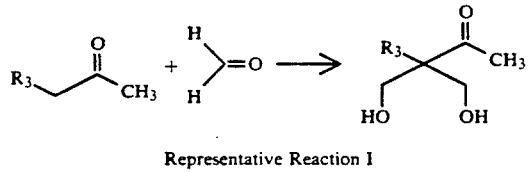

Representative Reaction I

REACTION EXAMPLE 1

3,3-BIS (HYDROXYMETHYL)-2-BUTANONE

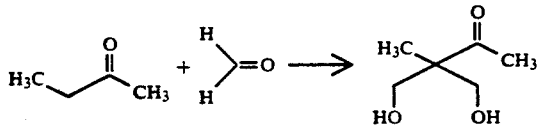

2-Butanone (216 parts) and 30% formalin (600 parts) are added to calcium hydroxide (1.9 parts) dissolved in water (1,300 parts). The mixture is stirred 6 hr at 10–15° C. and another portion of calcium hydroxide added (0.40 parts) followed by 6 hr of additional stirring. The mixture is neutralized and the solution extracted with ethyl acetate. The organic and aqueous layers are separated and the ethyl acetate removed to yield a residue at 95% of theory which is distilled in vacuo, b.p. 138–140° C. at 16 mm Hg. The distillate is recrystallized from a mixture of chloroform and petroleum ether, m.p. 60° C. Proton NMR and combustion analysis are consistent with those values predicted for the desired product. Combustion Analysis for $C_6H_{12}O_3$—Calculated: C, 54.5%; H, 9.2%. Found: C, 54.8%; H, 9.5%.

2-($R_1$)-2-($R_2$)-5-Acetyl-5-($R_3$)-1,3-dioxanes,

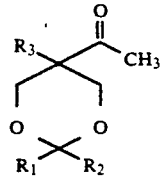
(3)

2-($R_1$)-2-($R_2$)-5-Acetyl-5-($R_3$)-1,3-dioxanes, where $R_1$ and $R_2$ are the same or different and can be, but not necessarily limited to; hydrogen, methyl, ethyl, higher or branched alkyl, aryl, substituted aryl, cycloalkyl, bicycloalkyl, spiro, etc., and $R_3$ can be alkyl ($C_1$-$C_{20}$), arylalkyl, etc., are either known compounds or can be prepared from appropriate [$R_3$]-3,3-bis(hydroxymethyl) methyl ketones or directly from suitably substituted methyl ketones. Suitable substitutions in the $R_3$ moiety being, but not necessarily limited to; methyl, ethyl, higher or branched alkyl, aryl, substituted aryl, cycloalkyl, bicyclo, spiro, fused aromatic, alicyclic, fused alicyclic, etc.

Compounds having the general formula (3) are prepared by an acid catalyzed condensation of the carbonyl of an aldehyde or ketone or their chemical equivalents, i.e., acetal, cyclic acetal, ketal, cyclic ketal, di(alkyloxy)acetal such as 2-dimethoxypropane, polymeric aldehydes i.e., paraformaldehyde, paracetaldehyde or the like, with either an appropriate ($R_3$)-3,3-bis(hydroxymethyl) methyl ketone of the general formula (1), as shown in Representative Reactions II, III and IVa, or directly with a methyl ($R_3$)-ketone, as shown in Representative Reaction IVb.

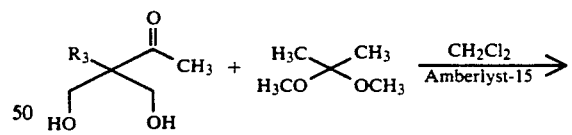

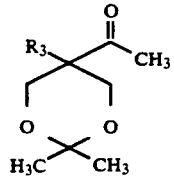

Representative Reaction II

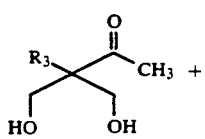

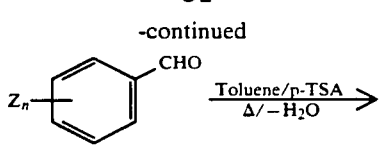

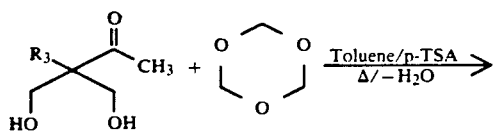

Representative Reaction III

The Z moieties to be selected from a list which includes, but is not necessarily limited to, such substituents as; nitro, alkyl, aryl, alkyloxy, aryloxy, halo, alkylamino, heterocyclic, hydroxy, cycloalkyl, a fused aromatic or cycloalkyl, or other substituted alicyclic moieties, etc. n is 0 to 3.

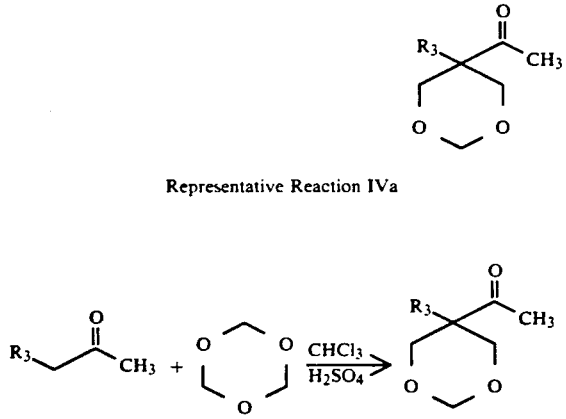

Representative Reaction IVa

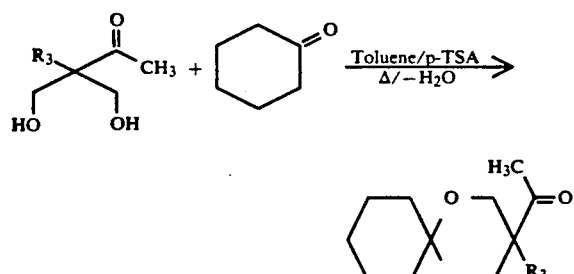

Representative Reaction IVb

Representative Reaction V can also apply to such cycloalkanones as cyclopentanone, cyclohexanone and higher cycloketones.

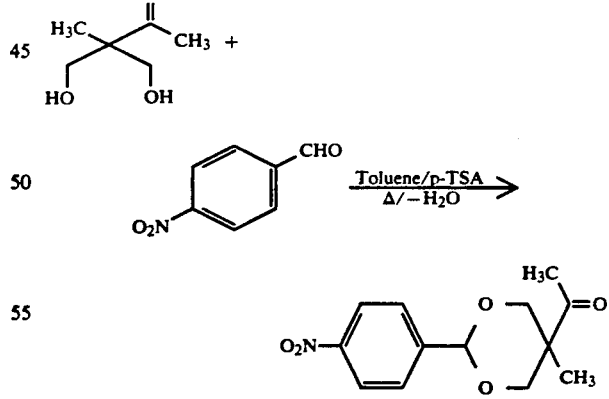

Representative Reaction V

The condensation reaction is perform ed in an inert solvent, in the presence of an acid catalyst, with heating or cooling as necessary. Exemplary catalysts include, but are not necessarily limited to, concentrated sulfuric acid, p-toluenesulfonic acid (p-TSA), Amberlyst-15 ® (strongly acid) ion exchange resin, Nafion ® or Lewis acids. Suitable inert solvents are hydrocarbons such as benzene and toluene or halocarbons such as chloroform or dichloromethane.

REACTION EXAMPLE 2

5-ACETYL-2,2,5-TRIMETHYL-1,3-DIOXANE

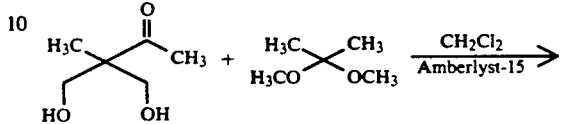

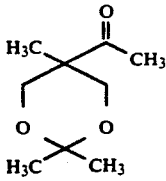

2,2-Dimethoxypropane (418 parts), 3,3-bis(hydroxymethyl)-2-butanone (265 parts) and Amberlyst-15 ®, (40 parts) are combined in dichloromethane (1,320 parts) and the resultant suspension stirred vigorously at room temperature, ca. 1 hr. The spent resin is separated from the solution by filtration and the residual solvents removed in vacuo to yield a pale straw-colored liquid which can solidify upon standing. Yield is 87% of theory and analytical samples are recrystallized from ethyl ether, m.p. 48-50° C. Proton NMR and combustion analysis are consistent with those values predicted for the desired product. Combustion Analysis for $C_9H_{16}O_3$—Calculated: C, 62.8%; H, 9.4%. Found: C, 62.0%; H, 9.0%.

REACTION EXAMPLE 3

5-ACETYL-5-METHYL-2-(4-NITROPHENYL)-1,3-DIOXANE 3,3-bis(Hydroxymethyl)-2-butanone (39.7 parts) and 4-nitrobenzaldehyde (30.2 parts) are combined in toluene (300 parts) containing p-toluenesulfonic acid, (p-TSA), (1.0 part) and the mixture held under reflux until a theoretical amount of water is removed by a Dean-Stark moisture trap. The solution is concentrated in vacuo and the residue washed once with dilute sodium bicarbonate solution. The product is recrystallized from ethyl acetate-heptane mixed solvent to give colorless needles, m.p. 101-102.5° C. Proton NMR and combustion analysis are consistent with those values predicted for the desired product. Combustion Analysis for $C_{13}H_{15}NO_5$—Calculated: C, 58.9%; H, 5.7%; N, 5.3%. Found: C, 59.0%; H, 5.8%; N, 5.4%.

REACTION EXAMPLE 4

5-ACETYL-5-METHYL-1,3-DIOXANE

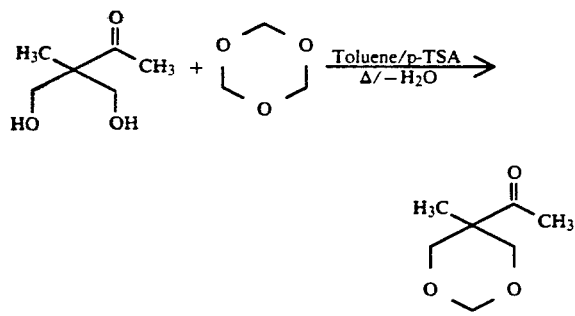

A solution of 3,3-bis(hydroxymethyl)-2-butanone (66.1parts) and s-trioxane (27 parts) in toluene (250 parts) containing p-toluenesulfonic acid (1.9 parts) is held under reflux while water of reaction is continuously removed (ca. 0.5 hr) by a Dean-Stark trap. The solution is cooled, neutralized by stirring with solid sodium bicarbonate and filtered Toluene is removed in vacuo and the residue distilled at 50–55° C. and 0.6 mm Hg. Proton NMR and combustion analysis are consistent with those values predicted for the desired product. Combustion Analysis for $C_7H_{12}O_3$—Calculated: C, 58.3%; H, 8.4%. Found: C, 57.9%; H, 8.2%.

REACTION EXAMPLE 5

5-(N-OCTYL)-5-ACETYL-1,3-DIOXANE

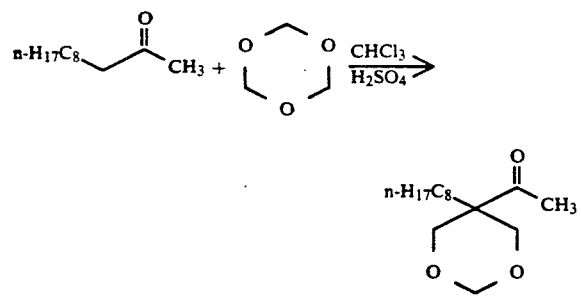

2-Undecanone (170.3 parts) and s-trioxane (45 parts) are combined in chloroform (1,500 parts) containing concentrated sulfuric acid (10 parts) and the reaction held under reflux, ca. 1 hr. The reaction is cooled and the organic phase subsequently washed with water, neutralized with aqueous sodium bicarbonate solution and dried over magnesium sulfate. The reaction solvent is removed in vacuo and the residual oil distilled under vacuum, b.p. 128–135° C. and 1.0 mm Hg, to give the final product. Proton NMR and combustion analysis are consistent with those values predicted for the desired product. Combustion Analysis for $C_{14}H_{26}O_3$—Calculated: C, 69.4%; H, 10.8%. Found: C, 69.9%; H, 11.0%.

REACTION EXAMPLE 6

METHYL 2,2,5-TRIMETHYL-β-OXO-1,3-DIOXANE-5-PROPANOATE

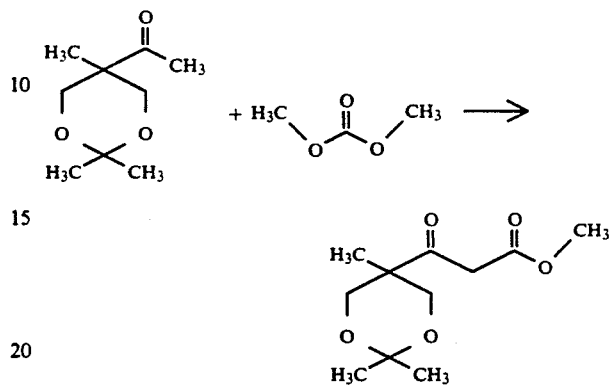

Washed sodium hydride (100 parts) is dispersed in a mixture of dry tetrahydrofuran (900 parts) and dimethyl carbonate (900 parts). The metal hydride is activated by a dropwise addition of anhydrous methanol (2 parts) followed by addition of a few parts of 5-acetyl-2,2,5-trimethyl-1,1,3-dioxane in tetrahydrofuran with constant stirring under an inert atmosphere. The reaction mixture is heated to reflux (constant stirring in an inert atmosphere) and thusly maintained while 5-acetyl-2,2,5-trimethyl-1,3-dioxane (172 parts) dissolved in tetrahydrofuran (800 parts) is added dropwise (ca. 0.5 hr). Reflux is maintained after complete addition of the 1,3-dioxane, ca. 1 hr. The reaction is allowed to cool and anhydrous methanol (100 parts) carefully added to the mixture followed by glacial acetic acid (150parts). Both methanol and acetic acid are added in a dropwise manner, under an inert atmosphere, with constant stirring and cooling as necessary. The reaction mixture is poured into water (1,000 parts) and the aqueous product extracted with ligroine. The ligroine extract is separated, washed with saturated sodium bicarbonate solution, dried over anhydrous magnesium sulfate, filtered and flash evaporated in vacuo to yield a crude product (203 parts) as a brown colored mobile oil which is purified by distillation to yield a water white liquid (130 parts, 57% of theory), b.p. 102–105° C. Proton NMR and combustion analysis were consistent with those values predicted for the desired product. Combustion Analysis for $C_{11}H_{18}O_5$—Calculated: C, 57.4%; H, 7.9%. Found: C, 57.7%; H, 8.0%.

REACTION EXAMPLE 7

N-(5-NITRO-2METHOXYPHENYL)-2,2,5-TRIMETHYL-β-OXO-1,3-DIOXANE-5-PROPANAMIDE

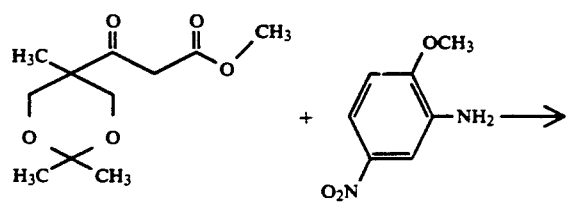

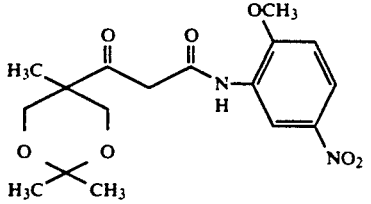

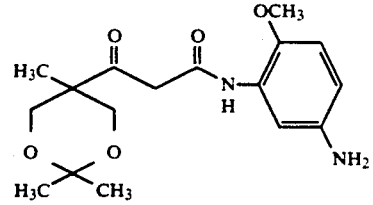

2-Methoxy-5-nitroaniline (63 parts) and methyl 2,2,5-trimethyl-β-oxo-1,3-dioxane-5-propanoate (90 parts) are dispersed in n-octane (500 parts) and m-xylene (100 parts). The mixture is stirred vigorously while methanol is removed by a slow distillation under an inert atmosphere. Additional m-xylene is added as needed to replenish the reaction solvent as it co-distills with methanol of reaction. After the solution is allowed to cool slowly with vigorous stirring, a yellow-orange solid resulted, ca. 2 hr. The precipitate is dissolved in ethyl ether and the ethereal solution extracted with dilute hydrochloric acid, washed once with dilute sodium bicarbonate, once with water, the organic layer separated from the aqueous layer, dried and the excess solvent removed in vacuo. The residue is recrystallized from ethyl alcohol, m.p. 113-115° C. Proton NMR and combustion analysis were consistent with those values predicted for the desired product. Combustion Analysis for $C_{17}H_{22}N_2O_7$—Calculated: C, 55.7%; H, 6.1%; N, 7.7%. Found: C, 55.6%; H, 6.1%; N, 7.5%.

REACTION EXAMPLE 8

N-(5-AMINO-2-METHOXYPHENYL)-2,2,5-TRIMETHYL-β-OXO-1,3-DIOXANE-5-PROPANAMIDE

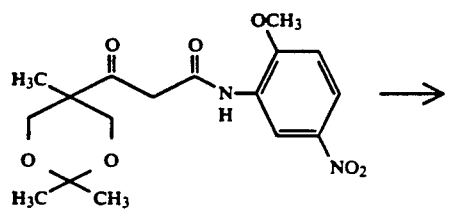

N-(5-Nitro-2-methoxyphenyl)-2,2,5-trimethyl-β-oxo-1,3-dioxane-5-propanamide (22parts) are dissolved in dry tetrahydrofuran (250 parts) and placed in a Parr bottle. The nitro compound is hydrogenated at low pressure and at ambient conditions in a Parr apparatus over Pd-C catalyst (2.5 parts) for 3.5 hr. Thin layer chromatography is used to monitor reaction completion which appears to be quantitative with no other products except the desired amine. The reaction product is carried to the next synthesis without purification other than filtration to remove spent catalyst.

REACTION EXAMPLE 9

N-[5-[[4-[2,4-BIS(1,1-DIMETHYLPROPYL)-PHENOXY]-1-OXOBUTYL]AMINO]-2-METHOXYPHENYL]-2,2,5-TRIMETHYL-β-OXO-1,3-DIOXANE-5-PROPANAMIDE

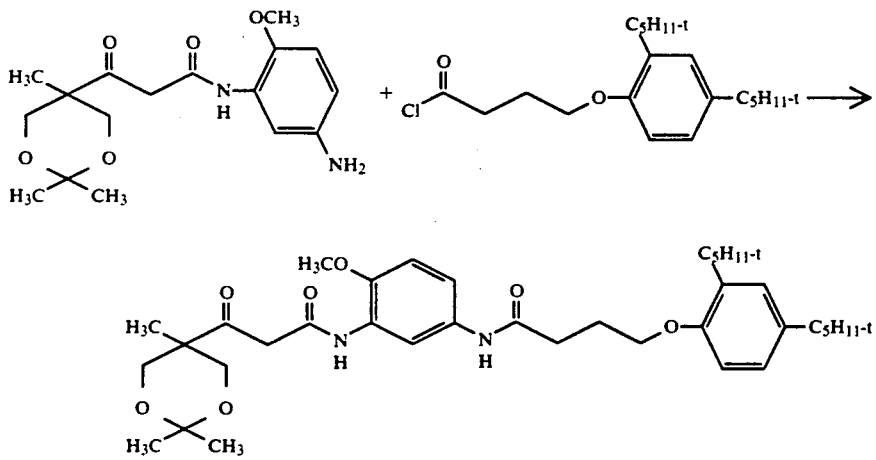

N,N-dimethylaniline (8.0 parts) and N-(5-amino-2-methoxyphenyl-2,2,5-trimethyl-β-oxo-1,3-dioxane-5-propanamide (20 parts) are combined in tetrahydrofuran (250 parts). γ-(2,4-di-tert-Amylphenoxybutyryl)-chloride (20.4 parts) dissolved in tetrahydrofuran (25 parts) is subsequently added dropwise to the stirred solution of amino compound, ca. 1 hr. The mixture is quenched in cold water (750 parts) containing concentrated hydrochloric acid (25 parts). The aqueous solution is extracted with ethyl ether and the ethereal extract washed once with dilute sodium bicarbonate solution and once with water. The ether extract is dried, filtered and flash evaporated to give a white, glass-like solid foam which is recrystallized from mixed ethyl acetate and heptane, m.p. 128-129.5ʳ C. Yield is 88.9% of theory. Proton NMR and combustion analysis were consistent with those values predicted for the desired product. Combustion Analysis for $C_{37}H_{54}N_2O_7$—Calculated: C, 69.6%; H, 8.5%; N, 4.4%. Found: C, 69.6%; H, 8.4%; N, 4.5%.

REACTION EXAMPLE 10

N-[5-[[4-[2,4-BIS(1,1-DIMETHYLPROPYL)-PHENOXY]-1-OXOBUTYL]AMINO]-2-METHOXYPHENYL]-α-CHLORO-2,2,5-TRIMETHYL-β-OXO-1,3-DIOXANE-5-PROPANAMIDE

REACTION EXAMPLE 11

N-[5-[[4-[2,4-BIS(1,1-DIMETHYLPROPYL)-PHENOXTY]-1-OXOBUTYL]AMINO]-2-METHOXYPHENYL]-2,2,5-TRIMETHYL-β-OXO-α-[4-[[4-(PHENYLMETHOXY)PHENYL]SULFONYL]PHENOXY]-1,3-DIOXNE-5-PROPANAMIDE

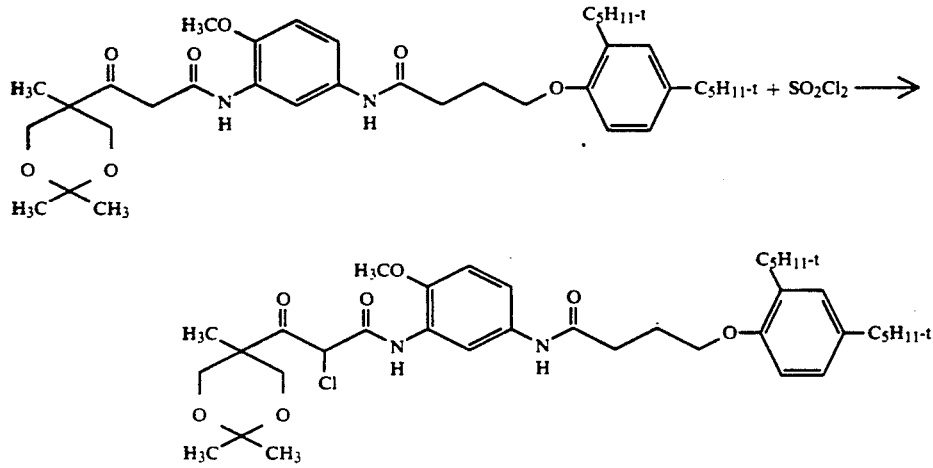

The β-ketoamide (19.2 parts) of Reaction Example 9

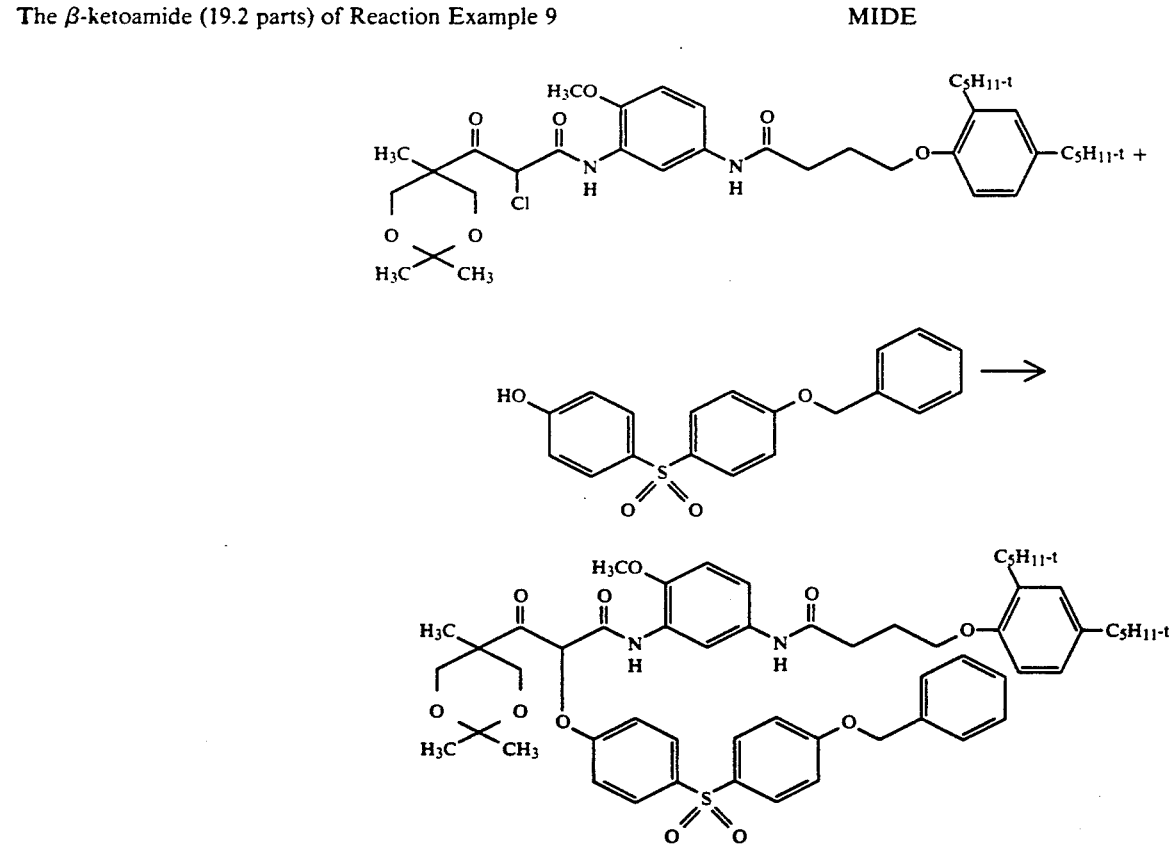

is dissolved in dichloromethane (350 parts) and treated with sulfuryl chloride (4.35 parts) by a dropwise addition at room temperature with constant stirring. After addition is complete the solution is stirred, ca. 1 hr, and subsequently evaporated in vacuo to yield a colorless, glass-like foam which is used as such in subsequent reactions.

A mixture of the α-chloro-β-ketopropanamide (16.8 parts) from Reaction Example 10 and 4-[[4-(phenylmethoxy)phenyl]sulfonyl]phenol (8.5 parts) and triethylamine (2.8 parts) is held under reflux, ca. 3.5 hr, after which time the mixture is poured into ice water (600 parts) containing concentrated hydrochloric acid (10 parts). The precipitate which resulted is collected, washed well with water and allowed to air dry. The crude solid is dissolved in ethyl ether followed by addition of heptane to the turbid point. White microcrystals separated from the solution upon standing, m.p. 110°–112° C. Yield is 68% of theory. Proton NMR and combustion analysis are consistent with those values predicted for the desired product. Combustion Analysis for $C_{56}H_{68}N_2O_{11}S$—Calculated: C, 68.8%; H, 7.0%; N, 2.9%; S, 3.3%. Found: C, 68.4%; H, 6.9%; N, 2.9%; S, 3.3%.

REACTION EXAMPLE 12

N-[5-[(HEXADECYLSULFONYL)AMINO]-2-METHOXYPHENYL]-2,2,5-TRIMETHYL-β-OXO-1,3-DIOXANE-5-PROPANAMIDE

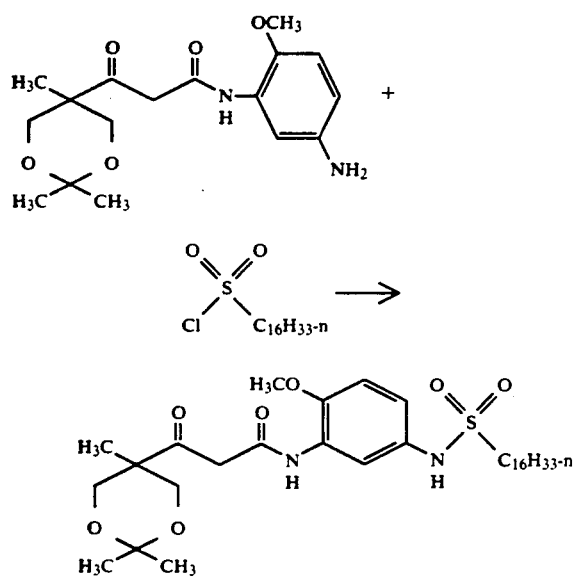

The amine product of Reaction Example 8, N-(5-amino-2-methoxyphenyl)-2,2,5-trimethyl-β-oxo-1,3-dioxane-5-propanamide, (18.5 parts) and N,N-dimethylaniline (8.5 parts) are combined in tetrahydrofuran (250 parts) and a solution of 1-hexadecylsulfonyl chloride (17.9 parts) dissolved in tetrahydrofuran (25 parts) is added dropwise with stirring, ca. 0.5 hr. The reaction is allowed to stand several hours and subsequently poured into cold water (600 parts) containing concentrated hydrochloric acid (5 parts). The crude product is extracted with ethyl ether and the ethereal layer washed once with sodium bicarbonate solution, once with water, dried over magnesium sulfate, filtered and subsequently flash evaporated in vacuo to give a light tan product in 90% of theoretical yield. Analytical samples are crystallized from ethyl alcohol, m.p. 83°–85° C. Proton NMR and combustion analysis are consistent with those values predicted for the desired product. Combustion Analysis for $C_{33}H_{56}N_2O_6S$—Calculated: C, 65.1%; H, 9.3%; N, 4.6%; S, 5.3%. Found: C, 65.6%; H, 9.1; N, 4.4%; S, 5.0%.

APPLICATION EXAMPLE

Preparation Of photographic element

Single layer photographic elements were prepared by coating a cellulose acetate-butyrate film support with a photosensitive layer containing a silver bromide emulsion at 70.2 and 140.4 mg/ft² for 2 and 4 equivalent couplers, respectively, gelatin at 350 mg/ft² and an image coupler (0.20 mmol/ft²) dispersed in half its weight of dibutyl phthalate. The photosensitive layer was overcoated with a layer containing gelatin at 250 mg/ft² and bis vinylsulfonyl methyl ether hardener at 2.0 weight percent based on total gel.

Samples of each element were exposed imagewise through a stepped density test object and processed at 100° F. employing the following color developing solution, then stopped with a low pH bath, bleached, fixed, washed and dried to produce stepped colored images.

| Color Developer Solution (2') | |
|---|---|
| $K_2CO_3$ | 37.50 g |
| $Na_2SO_3$ | 4.25 g |
| KI | 0.02 g |
| NaBr | 1.30 g |
| Hydroxylamine-Sulfate | 2.00 g |
| 4-Amino-3-methyl-N-ethyl N-β-hydroxyethylaniline sulfate | 3.55 g |
| Water to make 1 liter, pH 10.0 | |
| Low pH Bath: 3% Acetic Acid (30") | |
| Wash (2') | |
| Bleach (4') | |
| Ammonium Bromide | 150.00 g |
| Ammonium ferric EDTA (1.56N) | 175 ml |
| Acetic Acid | 9.5 ml |
| Sodium Nitrate | 35.00 g |
| Water to make 1 liter, pH 6.0 | |
| Wash (3') | |
| Fix (4') | |
| Ammonium thiosulfate (58%) | 214.00 g |
| (Ethylenedinitrilo)tetra-acetic acid, di-Na+ salt | 1.29 g |
| Sodium Metabisulfite | 11.00 g |
| NaOH (50%) | 4.70 g |
| Water to make 1 liter, pH 6.5 | |
| Wash (3') | |

Densitometry in the appropriate color maximum density (Dmin and Dmax) and gamma defined as the maximum slope between any two adjacent density points.

The processed strips generated were then subjected to usual light fade and wet oven tests. The light fade tests were 1, 3 and 6 weeks 5.4 Klux SANS tests. The wet oven testing is done at 60° C./70%RH for 1, 2 and 6 weeks. The compounds are listed in Table 4. Some of the couplers of the invention enable improved light stability and/or heat stability.

TABLE 4

| Coupler # | $D_{max}$ | $D_{min}$ | γ | $\lambda_{max}$ (nm) |
|---|---|---|---|---|
| P-I | 2.52 | 0.06 | 0.77 | 452 |
| P-III | 1.06 | 0.05 | 0.40 | 450 |
| P-V | 1.10 | 0.06 | 0.43 | 449 |
| P-VI | 0.25 | 0.05 | 0.10 | 447 |
| D-3 | 2.84 | 0.06 | 0.80 | 446 |
| D-4 | 2.95 | 0.06 | 1.10 | 454 |
| D-5 | 2.46 | 0.05 | 0.83 | 452 |
| D-7 | 2.51 | 0.05 | 0.83 | 445 |
| D-8 | 2.18 | 0.06 | 0.80 | 445 |
| D-10 | 3.07 | 0.06 | 1.13 | 453 |
| D-12 | 2.51 | 0.06 | 0.90 | 454 |
| D-13 | 2.55 | 0.06 | 0.90 | 452 |
| D-14 | 2.66 | 0.07 | 1.27 | 448 |

KEY TO TABLES
Pivaloyl acetanilide-based couplers
P-I.
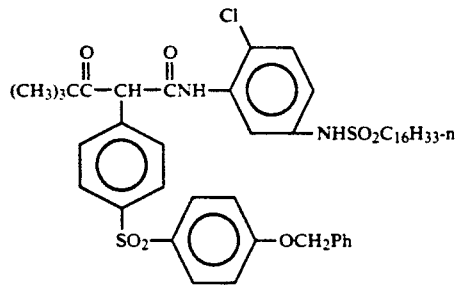
P-II.
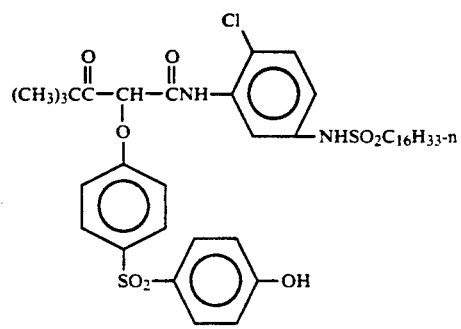
P-III.
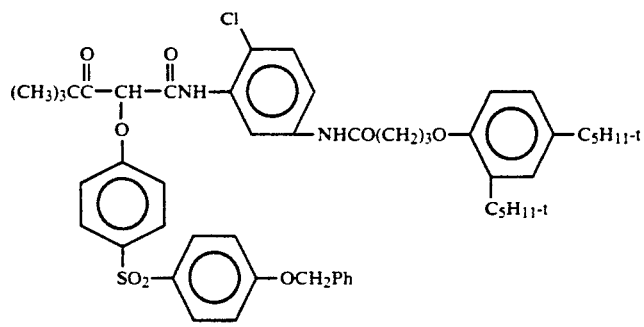
P-IV.
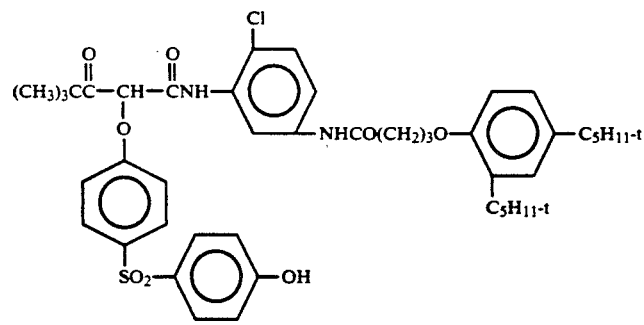
P-V.
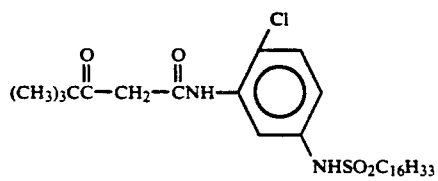

KEY TO TABLES-continued

Pivaloyl acetanilide-based couplers

P-VI.

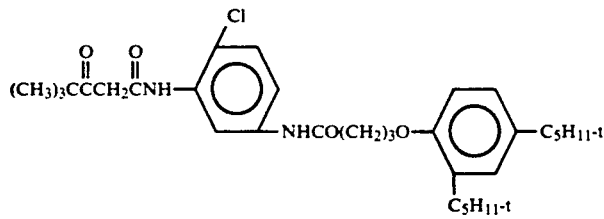

While the invention has been described in detail with respect to particular preferred embodiments, it should be understood that such description is presented by way of illustration and or limitation. Many changes and modifications within the scope of the present invention may be made without departing from the spirit thereof, and the invention includes all such modifications.

What is claimed is:

1. A color photographic element comprising a support bearing at least one photographic silver halide emulsion layer in association with an image dye-forming coupler, said coupler comprising:
   an active open-chain keto-methylene group,
   an anilide group attached to said keto-methylene group, said anilide group comprising an organic group capable of immobilizing the coupler in the layer in which it is contained; and
   a dioxane group attached to said keto-methylene group.

2. A color photographic element according to claim 1, wherein said dioxane is a 1,3-dioxane.

3. A color photographic element according to claim 2, wherein said keto-methylene group is substituted by a coupling-off group at the coupling position.

4. A color photographic element according to claim 1, wherein said coupler is a compound according to the formula I

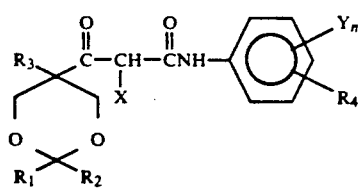

wherein
$R_1$ and $R_2$ are the same or different and may be hydrogen, alkyl, cycloalkyl, bicycloalkyl or aryl,
$R^3$ is alkyl, aryl, arylalkyl, or a ballast group,
X is hydrogen or a coupling off group,
Y and $R_4$ are the same or different and may be hydrogen, alkyl, O-alkyl, S-alkyl, $SO_2$-alkyl, $SO_2NH$-alkyl, $SO_2NH$-aryl, NHCONH-alkyl, NHCONH-aryl, NHCO-alkyl, $CO_2$-alkyl, O-aryl, $SO_2$-aryl, $SO_2N$(alkyl)-aryl, NHCO-aryl, $CO_2$-aryl, $O(CH_2CH_2O)_{1-4}H$, COOH, Cl, F, CN, $CF_3$ or $NO_2$, or $R_4$ can be a ballast group, and
n is 0-3.

5. A color photographic element according to claim 4, wherein said coupling-off group is selected from the group consisting of

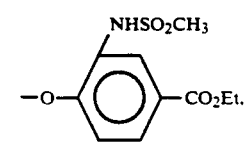

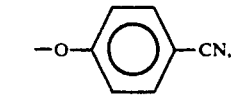

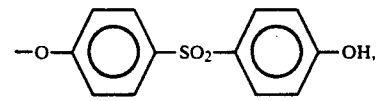

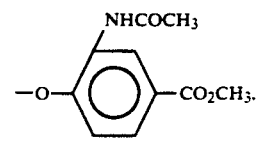

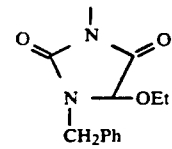

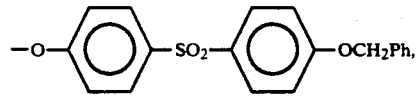

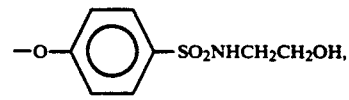

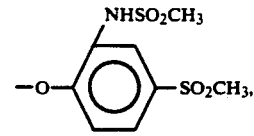

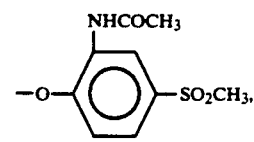

-continued and

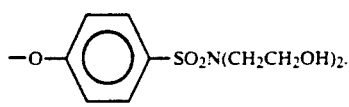

6. A color photographic element according to claim 4, wherein $R_1$ and $R_2$ are selected from the group consisting of hydrogen and methyl.

7. A color photographic element according to claim 4, wherein $R_3$ is selected from the group consisting of methyl and straight-chain alkyl.

8. A color photographic element according to claim 4, wherein $R_1$ and $R_2$ are both hydrogen.

9. A color photographic element according to claim 6, wherein $R_1$ and $R_2$ are both methyl.

10. A color photographic element according to claim 7, wherein $R_3$ is $C_8H_{17}$.

11. A color photographic element according to claim 7, wherein $R_3$ is $C_{12}H_{25}$.

12. A color photographic element according to claim 7, wherein $R_3$ is methyl.

13. A color photographic element according to claim 4, wherein $R_4$ is selected from the group consisting of $NHSO_2C_{16}H_{33}$-n, and

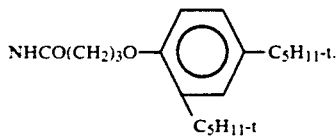

14. A color photographic element comprising a support bearing at least one photographic silver halide emulsion layer in association with an image dye-forming coupler wherein the coupler is a yellow image dye-forming 1,3-dioxane-5-carbonyl acetanilide coupler.

15. A color photographic element according to claim 14, wherein the element is a reversal film and the coupler is a four-equivalent yellow coupler represented by the formula III

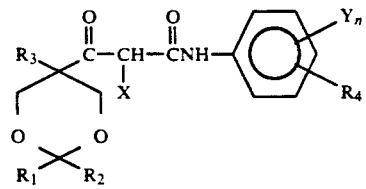

wherein
$R_1$ and $R_2$ are the same of different and may be hydrogen, alkyl, cycloalkyl, bicycloalkyl, aryl or a ballast group,
$R_3$ is alkyl, aryl or a ballast group,
X is hydrogen
Y is hydrogen, alkyl, O-alkyl, S-alkyl, $SO_2$-alkyl, $SO_2H$-alkyl, $SO_2NH$-aryl, NHCONH-alkyl, NHCONH-aryl, NHCO-alkyl, $CO_2$-alkyl, O-aryl, $SO_2$-aryl, $SO_2N$(alkyl)-aryl, NHCO-aryl, $CO_2$-aryl, $O(CH_2CH_2O)_{1-4}H$, COOH, Cl, F, CN, $CF_3$ or $NO_2$,
$R_4$ is a ballast group,
n is 0-3.

16. A color photographic element according to claim 14, wherein the element is a color negative film or color paper and the coupler is a two-equivalent formula II:

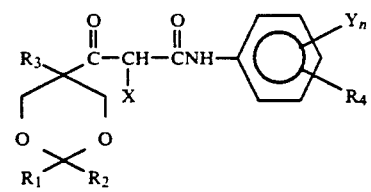

wherein
$R_1$ and $R_2$ are the same or different an may by hydrogen, alkyl, cycloalkyl, bicycloalkyl, aryl or a ballast group,
$R_3$ is alkyl, aryl or a ballast group.
X is a coupling-off group,
Y is hydrogen, alkyl, O-alkyl, S-alkyl, $SO_2$-alkyl, $SO_2NH$-alkyl, $SO_2NH$-aryl, NHCONH-alkyl, NHCONH-aryl, NHCO-alkyl, $CO_2$-alkyl, O-aryl, $SO_2$-aryl, $SO_2N$(alkyl)-aryl, NHCO-aryl, $CO_2$-aryl, $O(CH_2CH_2O)_{1-4}H$, COOH, Cl, F, CN, $CF_3$ or $NO_2$,
$R_4$ is a ballast group,
n is 0-3.

* * * * *